(12) United States Patent
Van Agthoven et al.

(10) Patent No.: US 7,968,279 B2
(45) Date of Patent: Jun. 28, 2011

(54) REFERENCE CONTROL FOR CELL BY CELL ANALYSIS

(75) Inventors: Andreas Van Agthoven, Marseilles (FR); Fabrice Malergue, Marseilles (FR)

(73) Assignee: Beckman Coulter, Inc., Brea, CA (US)

( * ) Notice: Subject to any disclaimer, the term of this patent is extended or adjusted under 35 U.S.C. 154(b) by 209 days.

(21) Appl. No.: 12/190,772

(22) Filed: Aug. 13, 2008

(65) Prior Publication Data

US 2010/0041011 A1 Feb. 18, 2010

(51) Int. Cl.
*A01N 1/02* (2006.01)
(52) U.S. Cl. .................................. 435/2; 436/10; 436/17
(58) Field of Classification Search ........ 435/2; 436/10, 436/17
See application file for complete search history.

(56) References Cited

U.S. PATENT DOCUMENTS

| | | | |
|---|---|---|---|
| 4,777,139 A | 10/1988 | Wong et al. | |
| 5,422,277 A * | 6/1995 | Connelly et al. | 436/10 |
| 5,478,722 A * | 12/1995 | Caldwell | 435/1.1 |
| 5,677,145 A | 10/1997 | Ryan | |
| 7,176,031 B2 * | 2/2007 | Li et al. | 436/63 |
| 7,361,513 B2 | 4/2008 | Ryan et al. | |
| 7,541,190 B2 * | 6/2009 | Van Agthoven et al. | 436/66 |
| 7,678,578 B2 * | 3/2010 | Van Agthoven et al. | 436/66 |
| 2003/0118637 A1 * | 6/2003 | Jordan et al. | 424/450 |
| 2004/0214243 A1 | 10/2004 | Burshteyn et al. | |
| 2006/0178294 A1 * | 8/2006 | Van Agthoven et al. | 514/2 |
| 2007/0020612 A1 * | 1/2007 | Van Agthoven et al. | 435/4 |
| 2007/0269460 A1 | 11/2007 | Inchauspe et al. | |

OTHER PUBLICATIONS

Campbell et al "Detection of Hemoglobin Variants in Erythrocytes by Flow Cytometry", Cytometry 35:242-248 (1999).
Goldstein et al "Glycated Hemoglobin: Methodologies and Clinical Applications", Clin Chem 32/10(B), B64-B70 (1986).
Sacks, David B. "Global Harmonization of Hemoglobin A1c", Clin Chem 51, No. 4, pp. 681-683 (2005).

* cited by examiner

*Primary Examiner* — Ralph Gitomer
(74) *Attorney, Agent, or Firm* — Merchant & Gould P.C.

(57) ABSTRACT

A reference control for cell by cell analysis on flow cytometric analyzers contains cellular analogs made of permeated blood cells containing therein aggregated intracellular proteins and preserved antigenic sites thereof, having cellular membrane permeable to antibodies and a suspension medium. The reference control is frozen after being prepared and thawed prior to use. The cellular analogs further contain a fluorescence marker therein. Further disclosed are a method of making the reference control and a method using the reference control, as an internal or stand-alone control, for measurements of cellular hemoglobin and cellular hemoglobin variant of a blood sample.

15 Claims, 5 Drawing Sheets

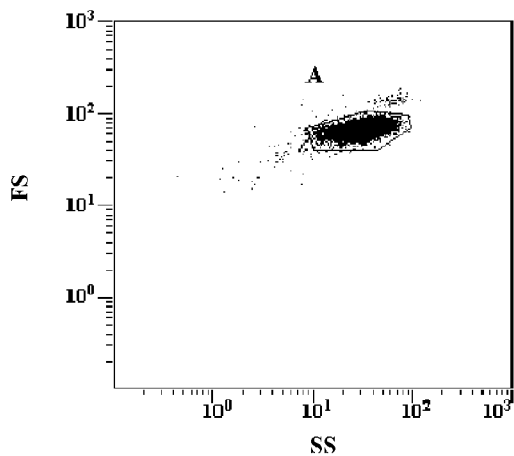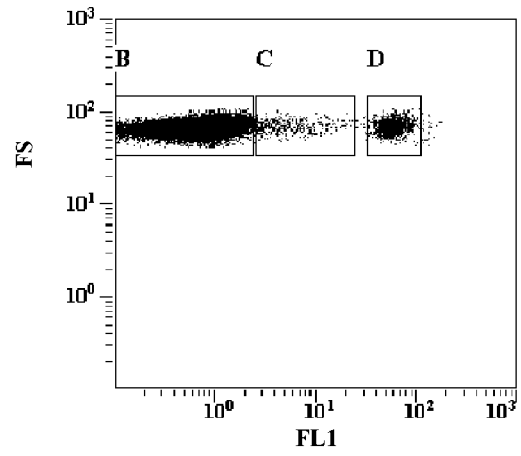
Fig. 1A
Fig. 1B
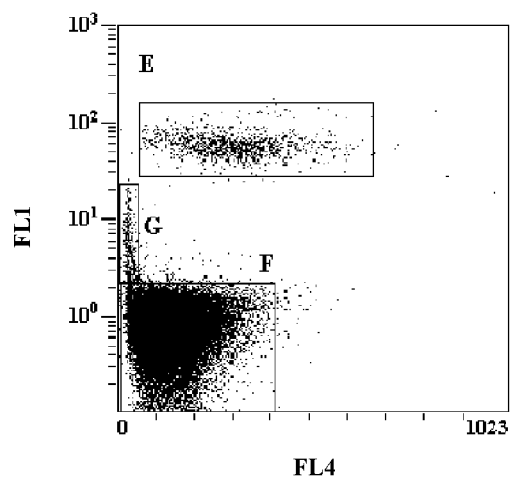
Fig. 1C

REFERENCE CONTROL FOR CELL BY CELL ANALYSIS

FIELD OF THE INVENTION

The present invention relates to a reference control containing cellular analogs made of permeated blood cells containing aggregated intracellular proteins and preserved antigenic sites, the method of making the reference control, and the method of using the reference control in cell by cell measurements of cellular components on flow cytometric analyzers.

BACKGROUND OF THE INVENTION

Quantitative measurement of cellular components in a cell by cell assay is usually performed on a cytometer or a hematological analyzer. A blood sample is prepared using specific reagent(s) and procedures and the presence of cellular components is determined using light scatter and fluorescence signals measured on these analyzers. Many physical or chemical factors can affect the ratio of the targeted cellular component present in the cell and the signal output of the measuring analyzer. Without a proper control or reference, it is difficult to obtain an accurate quantitative measurement of the cellular component. A reference control can be included in the measurements of a series of samples, as an external control; or a reference control can be added into each sample to be measured, as an internal control. In the latter case, it is necessary that the analyzer can differentiate between a cellular component from the reference control and the cellular component from the blood cells in the sample being measured.

A reference control can contain a synthetic particle, for example a latex bead covered with a targeted cellular component at a known amount. Other reference controls contain stabilized blood cells, having known amounts of targeted cellular components and being stable for a given period of time at a low non-freezing temperature.

Given the fact that signal variation is not only due to variations inherent to the measuring instrument, but also to variations in the preparation of the samples for the measurement, preferably the particles of a reference control behave similarly to the blood cells of the sample under the condition of sample preparation. In this respect, stabilized blood cells have an advantage over synthetic particles, however, the cellular components or the antigenic properties of the cellular components often deteriorate in the process of preparing the control cells or during their storage at a non-freezing temperature.

Freezing of cells and storage at ultra low temperatures would overcome the problem of degradation over time of the control cells. However, intracellular ice crystals damage the cellular membrane, and special precautions, for example, addition of protective agents such as glycerol or dimethylsulfoxide have to be taken to protect the cells through the freezing and thawing cycle. Even if undamaged, however, the treated cells often exhibit substantial modifications after the freezing and thawing cycle, which affect subsequent measurement. Moreover, the protective agents can also interfere with the assay to be performed.

Therefore, it is desirable that the cells used in the reference control have cell morphology comparable to the blood cells to be assayed and have preserved cellular components and preserved antigens of the cellular components to be measured, and that the cells of the reference control can undergo cycles of freezing and thawing without deterioration of cell morphology and antigens of the cellular components.

Furthermore, although a reference control with a known value of a parameter of interest can be used to correct inter assay variability, it is desirable to have an internal control containing cells in a labeled form to correct for intra assay variability as well as inter assay variability. The labeling of the cells in a reference control allows the measuring instrument to distinguish between the cells in the sample to be measured and the control cells added in the sample and to use these labeled cells as an internal control of the measurement process.

Moreover, in cell by cell assays for measuring intracellular components using antibodies or other molecular probes, it is necessary to permeate the cellular membrane so that the antibodies or other molecular probes can penetrate through the cellular membrane. For such assays, it is desirable to use a reference control containing cells that have their cellular membrane already permeated, which allows large probes such as antibodies to penetrate through.

U.S. Pat. No. 4,777,139 (to Wong et al) teaches a hematology control with red cell components of enhanced stability. Wong et al teach exposing washed red blood cells to an unsaturated aldehyde such as acrolein (propenal) under conditions sufficient to increase the stability of the cells without impairing the ability of a lysing reagent to lyse the cells. After treatment, the treated cells are washed and are suspended in a stabilizing suspension medium. The reference control is stored at low, non-freezing temperature. The membranes of these stabilized cells are not permeated.

The cellular hemoglobin of red blood cells is an important parameter for clinical diagnosis. On most hematology analyzers, total hemoglobin concentration of a blood sample is obtained by lysing red blood cells in a blood sample by a lytic reagent and measuring a chromogen formed by released hemoglobin molecules using spectrophotometric measurement. The mean corpuscular hemoglobin (MCH) of a blood sample is derived from the number of red blood cells (RBC) and total hemoglobin concentration of the blood sample. MCH is an average measurement of all red blood cells, it does not represent hemoglobin content of individual red blood cells.

In contrast, the measurement of cellular hemoglobin on a flow cytometer is a cell by cell measurement, which provides diagnostic information that is not available through MCH. Campbell et al. *Cytometry* 35, pp 242-248 (1999) have performed flow cytometric analysis of hemoglobin in individual red blood cells using a fluorescent anti-hemoglobin A antibody. Burshteyn et al. (U.S. Patent Application Publication No. 2004/0214243) have performed flow cytometric analysis of hemoglobin using an anti-pan hemoglobin antibody. Since red blood cells have a high concentration of hemoglobin, in order to measure the total cellular hemoglobin using antibodies, a large amount of fluorescently-labeled antibodies are required. Furthermore, there are potential artifacts due to steric hindrance of antibody binding or extinction of fluorescence due to high density of hemoglobin in the cell. Therefore, it is desirable to have a method that enables the measurement of total cellular hemoglobin without relying on the use of antibodies.

Identifying and/or quantifying variants and aberrant forms of hemoglobin are important for clinical diagnosis of various diseases, for example, sickle cell disease, thalassemia and diabetics. The measurement of hemoglobin $A_{1C}$ has been one of most frequently used hemoglobin variant measurement, and is an important clinical measure for diabetic patients.

It is known that about 90% of total hemoglobin is nonglycosylated. The major fraction of nonglycosylated hemoglobin is nonglycosylated HbA, referred to as HbA0. Glycated hemoglobin refers to a series of minor hemoglobin components that are formed via the attachment of various sugars to the hemoglobin molecule. The human erythrocyte is freely permeable to glucose. Within each erythrocyte, glycated hemoglobin is formed at a rate that is directly proportional to the ambient glucose concentration. The reaction of glucose with hemoglobin is nonenzymatic, irreversible and slow, so that only a fraction of the total hemoglobin is glycated during the life span of an erythrocyte (120 days). As a result, the measurement of glycated hemoglobin provides a weighted "moving" average of blood glucose levels that can be used to monitor long-term blood glucose levels, providing an index of the mean blood glucose concentration over the preceding 2 to 3 months. The most important clinical application of this is in the assessment of glycemic control in a diabetic patient.

Hemoglobin A1c (HbA1c) is one specific type of glycated hemoglobin and is the most important hemoglobin species with respect to diabetes. $Hb_{A1c}$ is approximately 3 to 6% of the total hemoglobin in nondiabetics, and 20% or greater in diabetes that is poorly controlled (Goldstein, et al., *Clin. Chem.* 32: B64-B70, 1986). The determination of the concentration of $Hb_{A1c}$ is useful in diagnosing and monitoring diabetes mellitus.

Several standard $Hb_{A1c}$ assay methods have been developed in the last few decades. One standard method of measuring HbA1c uses ionic-exchange high performance liquid chromatography (HPLC), which separates and analyzes $Hb_{A1c}$ and other minor hemoglobin components from hemoglobin HbA0 based upon the differences in charge density. Another chromatography method is boronate affinity chromatography, which uses a gel matrix containing immobilized boronic acid to capture the cis-diol group of glycated hemoglobin. In these methods, a blood sample is lysed first with a lytic reagent, and then formed hemolysate is used in the chromatography analysis.

A further $Hb_{A1c}$ assay method is based on immunoturbidimetry. In this method, a blood sample is lysed first with a lytic reagent, and the formed hemolysate is used in two separate measurements. The total hemoglobin concentration is measured by a colorimetric method. HbA1c concentration is measured using the turbidimetric immunoinhibition method, in which HbA1c antibodies in a reagent bind to HbA1c of the sample to form soluble antigen-antibody complexes. Poly-haptens from the reagent then bind with the excess antibodies and the resulting agglutinated complex is measured turbidimetrically. The turbidity of the sample mixture is inversely proportional to the concentration of HbA1c in the sample. The percentage of HbA1c of the sample is calculated using the total hemoglobin and the HbA1c concentration.

These standard HbA1c assay methods are bulk analyses of the average concentration of total hemoglobin and HbA1c percentage of the hemolysate obtained from all lysed red blood cells of a sample, including both mature red blood cells and reticulocytes. This result can only be used as an index of the mean blood glucose concentration over the preceding 2 to 3 months, it does not represent cellular HbA1c percentage of individual red blood cells, and does not provide information of HbA1c percentage between mature red blood cells and immature red blood cells. Therefore, these standard methods do not provide timely information on patient's response to medical treatments.

A number of HbA1c controls are available commercially. Most of these controls are in the form of lyophilized protein powders or hemolyzed liquid solutions, which are used for the above-described methods.

Recently, U.S. Pat. No. 7,361,513 (to Ryan et al.) teaches cellular controls for glycated hemoglobin $Hb_{A1c}$ measurement, suitable for use in ion exchange, or affinity chromatography and immunologic detection described above. Ryan et al. teach a method of preparing the reference control, which includes washing a blood sample; removing white blood cells and platelets from red blood cells; fixing the red blood cells with glutaraldehyde; washing and suspending the fixed red blood cells with a stabilizing diluent that contains glucose, sodium fluoride and soybean trypsin inhibitor. Ryan et al. teach this reference control being stable for 300 days at 6° C. and show its utility on several clinical chemistry analyzers that utilize ionic-exchange HPLC, boronate affinity chromatography, or immunoturbidimetry. Using these methods, as described above, the stabilized red blood cells in Ryan et al. are lysed first, then the total hemoglobin and total HbA1c concentration of all red blood cells from the control are measured. Ryan et al do not teach permeating cellular membrane of the fixed red blood cells to render them permeable to antibodies for cell by cell immunoassay on flow cytometer.

Based on the above, it is therefore desirable to provide a reference control containing cellular analogs that have permeated cellular membrane for cell by cell analysis of HbA1c, other hemoglobin variants, or other cellular components on flow cytometer. It is also desirable to have a reference control wherein the total cellular hemoglobin of the cellular analogs can be measured in one step together with a hemoglobin variant. It is further desirable to have a reference control that has labeled cellular analogs so that the analogs can be readily identified and differentiated from blood cells to be measured using commonly available detection devices. Moreover, it is desirable to have a reference control that can be frozen and thawed for long term storage, while maintaining the cellular components of the cellular analogs to be measured, for example, maintaining protein antigenic sites. Furthermore, it is also desirable to have a reference control that is resistant to freeze-thaw treatment without using protective agents that may interfere with the assay to be performed.

SUMMARY OF THE INVENTION

In one aspect, the present invention is directed to a reference control for cell by cell analysis on flow cytometric analyzers. The reference control comprises cellular analogs made of permeated blood cells containing therein aggregated intracellular proteins and one or more preserved antigenic sites thereof, having cellular membrane permeable to an antibody, and a suspension medium. The reference control is frozen after being prepared and thawed prior to use. The cellular analogs maintain the preserved antigenic sites after being thawed.

In one embodiment, the reference control comprises labeled cellular analog that comprises a cellular marker bound to a cellular component of treated blood cells. In a particular embodiment, the cellular analogs are red cell analogs made of red blood cells comprising preserved antigenic sites of one or more hemoglobin variants.

In another aspect, the present invention is directed to a method of making the reference control of the present invention. The method comprises mixing a permeation reagent with blood cells and incubating formed permeation mixture for a period of time sufficient to cause aggregation of intracellular proteins within the blood cells while preserving antigenic sites thereof, and to render cellular membrane permeable to an antibody; adding a neutralization reagent to the permeation mixture to inhibit further reactions of the permeation reagent; washing the permeated blood cells with a washing solution to remove the permeation and neutralization reagents from permeated blood cells; suspending the permeated blood cells in a storage solution to form the reference control. Preferably, the reference control is frozen for storage, and is thawed prior to use.

In a further aspect, the present invention is directed to a method of using the reference control of the present invention in a cell by cell measurement of cellular components on a flow cytometric analyzer. In one embodiment, the method is directed to using a reference control for cellular hemoglobin measurement of a blood sample on a flow cytometric analyzer. The method comprises providing a reference control comprising red cell analogs made of treated red blood cells containing therein aggregated intracellular proteins, the reference control having a reference value of mean cellular hemoglobin; measuring cell by cell side scatter signals of the red cell analogs of the reference control on the flow cytometric analyzer; and using obtained side scatter signals and the reference value of the reference control to determine cellular hemoglobin of individual red blood cells of a sample to be measured.

The method can further comprise mixing said reference control with a permeation reagent; subsequently adding a neutralization reagent containing a fluorescently labeled antibody specific to said hemoglobin variant and allowing said antibody to bind to said hemoglobin variant within said red cell analogs; measuring cell by cell fluorescence signals of said red cell analogs of said reference control together with said measuring side scatter signals; and using obtained fluorescence signals and obtained side scatter signals, and a reference value of hemoglobin variant percentage of said reference control to determine a percentage of said hemoglobin variant of individual red blood cells of a sample to be measured. The hemoglobin variant comprises glycated hemoglobins, fetal hemoglobin, or aberrant forms of hemoglobin.

In a further embodiment, the method is directed to using a labeled reference control for cellular hemoglobin measurement of a blood sample on a flow cytometric analyzer. The method comprises mixing a volume of a blood with a permeation reagent to form a first sample mixture; adding a reference control containing red cell analogs and having a cellular hemoglobin reference value into said first sample mixture, said red cell analogs being made of treated red blood cells containing therein aggregated intracellular proteins and preserved antigenic sites of a hemoglobin variant, and having cellular membrane permeable to an antibody, and said red cell analogs comprising a fluorescent dye bound to cellular proteins; subsequently adding a neutralization reagent to form a second sample mixture; measuring cell by cell side scatter signals and fluorescence signals at a first wavelength of said red blood cells of said blood and said red cell analogs of said reference control on said flow cytometric analyzer; differentiating said red blood cells of said blood from said red cell analogs of said reference control using obtained fluorescence signals at said first wavelength; and determining cellular hemoglobin of said red blood cells using obtained side scatter signals of said red blood cells and said red cell analogs, and said cellular hemoglobin reference value of said reference control.

The method further comprises mixing said blood with a nucleic acid dye to stain RNA prior to said mixing said blood with said permeation reagent; differentiating reticulocytes from mature red blood cells of said blood and from said red cell analogs using said fluorescence signals at said first wavelength; and determining cellular hemoglobin of said reticulocytes and said mature red blood cells using said side scatter signals and said cellular hemoglobin reference value of said reference control.

Moreover, the neutralization reagent can further contain a fluorescently labeled antibody specific to said hemoglobin variant. The method further comprises incubating said second sample mixture to allow said labeled antibody bind to said hemoglobin variant in said reticulocytes and said mature red blood cells of said blood, and in said red cell analogs of said reference control; measuring cell by cell fluorescence signals at a second wavelength of said reticulocytes and said mature red blood cells of said blood, and in said red cell analogs of said reference control, together with measuring said side scatter signals and said fluorescence signals at said first wavelength; and determining a cellular percentage of said hemoglobin variant in said reticulocytes and said mature red blood cells, respectively, using fluorescence signals at said second wavelength and said side scatter signals, and a reference value of said hemoglobin variant percentage of said reference control.

The advantages of the present invention will become apparent from the following description taken in conjunction with the accompanying drawings showing exemplary embodiments of the invention.

BRIEF DESCRIPTION OF THE DRAWINGS

FIGS. 1A, 1B and 1C show scattergrams of forward scatter vs. side scatter, forward scatter vs. FL1, and FL1 vs. FL4 of a normal blood sample containing a labeled reference control that comprises the red cell analogs made of a blood sample from a diabetic patient, as described Example 3. In the three scattergrams, all axes are in logarithmic scales.

DETAILED DESCRIPTION OF THE INVENTION

Figure 2A:
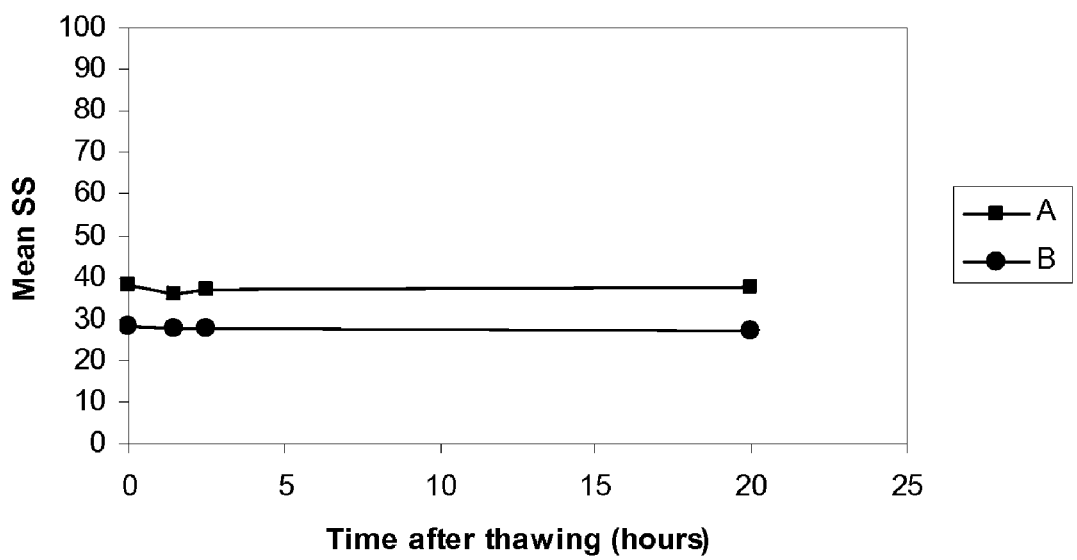
FIGS. 2A and 2B show mean side scatter and mean FL4 of the red blood cells of a normal human blood sample (A) and the internal control (B), respectively, obtained at different times after thawing of the reference control, as described in Example 4.

In one aspect, the present invention provides a reference control containing cellular analogs for cell by cell analysis on flow cytometric analyzers and the method of making.

In one embodiment, the reference control comprises cellular analogs made of permeated blood cells containing therein aggregated intracellular proteins and one or more preserved antigenic sites thereof and having cellular membrane permeable to one or more antibodies, and a suspension medium. The reference control is frozen after being prepared, and is thawed prior to use.

In one particular embodiment, the reference control comprises red cell analogs made of permeated red blood cells that contain therein aggregated intracellular proteins and one or more preserved antigenic sites of hemoglobin variants, having cellular membrane permeable to one or more antibodies specific to antigenic sites of hemoglobin variants.

The method of making the reference control of the present invention is described now in detail. In one embodiment, the method comprises following processing steps:
(a) mixing a permeation reagent with blood cells and incubating formed permeation mixture for a period of time sufficient to cause aggregation of intracellular proteins within the blood cells while preserving antigenic sites thereof, and render cellular membrane permeable to one or more antibodies;
(b) adding a neutralization reagent to the permeation mixture to inhibit further reactions of the permeation reagent;
(c) washing the permeated blood cells with a washing solution to remove the permeation and neutralization reagents from the treated or permeated blood cells;
(d) suspending the permeated blood cells in a storage solution to form the reference control in a form of analog suspension.

For long term storage, the reference control is frozen after being prepared and remained frozen during shipping, as further described hereinafter. The reference control can be thawed naturally at room temperature by the user prior to use. The reference control can be used as an internal or external control for cell by cell analysis on flow cytometric analyzers, as described hereinafter.

The blood cells are typically collected from peripheral blood (also referred to as whole blood) of a suitable subject, including, but not limited to, mammal, avian or reptile. For the purpose of measuring a specific clinical condition, the blood is preferably collected from human, including both normal subject and patients who have been diagnosed with a specific clinical condition of interest, therefore, a cellular component of interest, such as an antigen, is present or elevated. For example, for making a reference control for measurement of HbA1c, a blood can be collected from a patient diagnosed with diabetes. For a reference control for measurement of sickle cell anemia or thalassemia, a blood can be collected from a patient suffering from respective diseases. In other situations, a blood can be collected from a subject having an abnormally low cellular component of interest.

The blood is collected into containers containing an anticoagulant. Ethylenediamine tetraacetic acid (EDTA) or other commonly used anticoagulants, such as heparin and sodium citrate can be used. The blood can be stored at 4° C., prior to being treated, preferably for no more than three days.

Prior to mixing with the permeation reagent, the blood cells of interest can be isolated using the techniques known in the art, for example, centrifugation, dialysis or other suitable methods. For example, when white cell analogs are prepared, white blood cells can be separated from the red blood cells by separating the buffy coat after centrifugation of a whole blood. It has been found, however, when red cell analogs are prepared for cellular hemoglobin measurement using the process described above, the white blood cells and platelets do not need to be removed from the red blood cells, because in a cell by cell analysis using light scatter and/or fluorescence measurements the platelets and white blood cells can be differentiated from the red cell analogs using the light scatter and/or fluorescence signals.

Example 2 illustrates an exemplary process of preparing labeled red cell analogs using a whole blood with the method of the present invention described above. It is noted that the preparation of the reference control is specifically described in a process of preparing a labeled red cell analog, which will be described in more detail later, however, the process, other than steps related to labeling, can be used for preparing unlabeled cellular analogs. It is further noted that when cellular analogs without a fluorescence label are prepared, the blood cells do not need to be washed, and a whole blood can be used directly for preparing the reference control. Moreover, the process can also be used for preparing other cell analogs, such as white blood cells, or specific subpopulations of white blood cells.

For the purpose of measuring cellular hemoglobin, preferably the labeled red blood cells are also exposed to a sphering reagent to sphere the red blood cells, prior to being treated with the permeation reagent. It is noted that the sphering step is optional. Moreover, when a white blood analog is prepared, such a step is not needed.

A permeation reagent used herein is also referred to as a cell permeabilization and stabilization reagent, and its function in permeating cellular membrane and preserving cellular components for flow cytometric measurements has been described in U.S. 20060178294 A1, which is herein incorporated by reference in its entirety.

In one embodiment, the permeation reagent is an aqueous solution comprising N-acyl sarcosine or a salt thereof represented by the following molecular structure:

wherein $R_1$ is an alkyl or alkylene group having 8 to 18 carbon atoms, and $X_1$ is H, $Na^+$, or $K^+$, and one or more pH adjusting agents to adjust pH of the reagent less than 7. The permeation reagent is preferably slightly acidic, with a pH in a range from about 4 to about 6. More preferably, pH of the reagent is from about 4.6 to about 5.6.

Preferably, the pH adjusting agent is a strong base or acid, therefore, a small quantity of the chemical can be used to adjust the pH within the desired range. In one preferred embodiment, N-acyl sarcosine free acid is used, and pyrrolidine, a strong organic base, or NaOH, a strong inorganic base, is used to adjust the pH between 4 and 6. If a N-acyl sarcosine salt is used, then a strong acid, such as HCl, can be used to adjust the pH. Furthermore, an organic buffer can be used to maintain the pH. In one exemplary embodiment, succinic acid is used, which has a $pKa_1$ of 4.19 and $pKa_2$ of 5.57.

The permeation reagent has a low ionic strength defined by a conductivity of less than 9.0 mS/cm. It has been found that upon exposing the cells to the permeation reagent, intracellular protein aggregation is more effective under a low ionic strength. For the purpose of the present invention, the desired ionic strength of the aqueous reagent composition is quantified by conductivity of the reagent. It is believed that intracellular protein aggregation is necessary to conserve cell integrity after permeation. When the ionic strength of the permeation reagent is too high, for example when the conductivity of the reagent is 9 mS/cm of higher, the reagent can no longer aggregate intracellular proteins, and the cells lose their integrity. Preferably, the permeation reagent has a conductivity of less than 3.0 mS/cm, more preferably less than 1.2 mS/cm. Since ionic compounds, such as salts, are the major contributors of ionic strength of an aqueous solution, it is preferred to have a low salt concentration in the permeation reagent.

N-acyl sarcosine, in a free acid form, and the salt thereof are commercially available. It is preferred to use the free acid form, which does not introduce metal ions into the permeation reagent. N-acyl sarcosine in a free acid form is not water soluble. It can be pre-dissolved in an ethanol solution, and then added into the aqueous solution. When pH of the permeation reagent is adjusted between 4 and 6 by a base, as a pH adjusting agent, N-acyl sarcosine free acid can be dissolved and is present in the form of anion in the solution.

Suitable examples of N-acyl sarcosine include N-oleoyl sarcosine, N-stearoyl sarcosine, N-lauroyl sarcosine, N-myristoyl sarcosine, N-cocoyl sarcosine, and salts thereof. Preferably, the alkyl or alkylene group of $R_1$ has 12 carbon atoms. In one preferred embodiment, N-lauroyl sarcosine is used.

The permeation reagent N-acyl sarcosine or the salt thereof is in amount sufficient to permeate cellular membrane sufficient to allow penetration of intracellular markers through the permeated membrane, while substantially preserving the cellular membrane structure and cellular constituents for specific bindings with their cellular markers for cell by cell analysis by flow cytometry. It has been found that concentration of N-acyl sarcosine can be in a range from about 0.01 mM to about 100 mM, preferably about 0.1 mM to about 10 mM, and more preferably about 1 mM to about 5 mM.

Optionally, the permeation reagent may further comprise an anionic surfactant represented by following molecular structure:

wherein $R_2$ is an alkyl or alkylene group having 8 to 18 carbon atoms; and $X_2$ is $Na^+$, $K^+$, $NH_4^+$, or $NH_2C(CH_2OH)_3$ (i.e., tris(hydroxymethyl)-aminomethane). Preferably, the alkyl or alkylene group of $R_2$ of the anionic surfactant has 12 carbon atoms. Suitable examples include sodium, potassium, ammonium and tris(hydroxymethyl)aminomethane lauryl sulfates. In a preferred embodiment, tris(hydroxymethyl)aminomethane lauryl sulfate is used, which is referred to as Tris lauryl sulfate hereinafter. Alkyl or alkylene sulfate can be in a range from about 0.01 mM to about 5 mM, preferably, from about 0.05 to about 2 mM.

Preferably, the permeation reagent further comprises one or more organic osmolality adjusting agents. Suitable examples of the osmolality adjusting agent include, but are not limited to, saccharide, ethylene glycol, dimethylsulphoxide, or glycerol. Preferably, saccharide or glycerol is used. The saccharide can be a polysaccharide, such as a disaccharide, or a monosaccharide. In one exemplary embodiment as shown in Example 1, sucrose is used. In the presence of organic osmolality adjusting agents, although the permeation reagent has very low ionic strength, it is only slightly hypotonic, and has an osmolality from about 240 to about 280 mOsm/kg $H_2O$.

Optionally, the permeation reagent further comprises a serum albumin, such as bovine serum albumin (BSA). Serum albumin enhances solubility of the surfactant in the aqueous solution, and is beneficial for long term use and storage of the permeation reagent.

Furthermore, the permeation reagent can further comprise one or more preservatives. Suitable examples include antimicrobials and antioxidants, for extension of shelf life of the permeation reagent. The preservative can be present in an amount that does not interfere with the function of the permeation reagent. In one embodiment, 5-chloro-2-methyl-4-isothiazolin-3-one and 2-methyl-4-isothiazolin-3-one are used as antimicrobials. Combinations of 5-chloro-2-methyl-4-isothiazolin-3-one and 2-methyl-4-isothiazolin-3-one manufactured by Rohm and Hass, Philadelphia, Pa., are available commercially under the trade name Proclin® 150 and Proclin® 300. Example 1 shows an exemplary composition of the permeation reagent of the present invention.

Preferably, the blood is mixed with the permeation reagent with a reagent to blood ratio of about 100:1 or higher. The formed permeation mixture is incubated for a period time sufficient to allow the reaction of the permeation reagent with the cells. Preferably, the incubation time is from about 1 minute to about 10 minutes, more preferably, from about 2 minutes to about 5 minutes.

It has been found that when mixed with blood cells, the permeation reagent effectively permeates cellular membrane to an extent that allows penetration of macromolecular intracellular markers, such as antibodies, into the cell for binding to an intracellular component for subsequent measurement. The permeation reagent causes intracellular protein aggregation within the cells, while preserves cellular components, such as intracellular and cell surface antigenic sites, DNA and RNA molecules, and cytoskeleton elements, for subsequent cell by cell analysis. Moreover, during the permeation treatment the red blood cells are also sphered by the permeation reagent, which enables measurement of red blood cells by light scatter measurements, without undesirable effects of heterogeneous cell shape and orientation.

For the purpose of the present invention, the term "cellular component" or "cellular constituent" includes cellular components inside the cells, and on the surface of the cellular membrane such as cell surface antigen sites. While the term "intracellular component" or "intracellular constituent" refers to a cellular component inside the cells, which includes, but is not limited to, intracellular proteins, such as hemoglobin and hemoglobin variants inside the red blood cells, cytoskeleton elements, DNA and RNA. The cytoskeleton elements include, but are not limited to, tubulin and spectrin. The term "cellular marker" used herein includes, but is not limited to, an antibody specific to an antigen site of an intracellular protein, a cell surface antigen site, or a cytoskeleton element; a dye such as a nucleic acid dye or a dye specific to cellular protein, and a nucleic acid probe specific to a DNA or a RNA molecule, such as an oligonucleotide probe. Preferably, the cellular marker is fluorescent or labeled with a fluorescent dye. Furthermore, the cellular marker specific to an intracellular component is referred to as an intracellular marker.

As described in U.S. 2006/0178294 A1, the permeation reagent causes precipitation of serum fraction, soluble cellular fraction (cytosol) and membrane fraction prepared from a whole blood. Particularly in the soluble cellular fraction, because of the presence of hemoglobin, strong aggregation and precipitation upon reacting with the permeation reagent occur, evidenced by a substantial increase of optical density of the sample mixture. As further shown in U.S. 2007/0020612 A1, intracellular protein aggregation of the blood cells is reflected by substantial increases of the side scatter signals of the red blood cells in whole blood samples exposed to the permeation reagent. On the other hand, however, as further shown in U.S. 2006/0178294 A1, the permeated blood cells maintain their antigenic sites and antibody binding specificity, for example, binding of tubulin of the red blood cells and lymphocytes to anti-tubulin-FITC antibody, binding of fetal hemoglobin to anti-HbF-FITC, and binding of fetal erythrocytes to extracellular marker anti-i-phycoerythrin (PE).

As described above, after exposing to the permeation reagent, a neutralization reagent is added into the permeation mixture to inhibit further reactions of the permeation reagent. The neutralization reagent is hypertonic and can have a pH of 7 or slightly above. When mixed with the permeation mixture, the neutralization reagent brings pH of the mixture to neutral, and increases the ionic strength of the mixture. As such, it effectively inhibits further reaction of the permeation reagent. It is believed that excessive reaction with the permeation reagent can result in too tight intracellular protein aggregation, which can result in masking of the antigenic sites of the proteins, and affect their binding to intracellular markers. The extent of the treatment of the blood cells by the permeation reagent can be controlled by the incubation time described above and by effective inhibition by the neutralization reagent.

The neutralization reagent comprises an osmolality adjusting agent and a buffer. Preferably, osmolality adjusting agent is one or more alkaline metal salt, preferably alkaline metal halides, such as sodium or potassium chloride. The osmolality of the neutralization reagent is preferably from about 800 to about 1,200 mOsm/kg $H_2O$. The buffer can be an organic or inorganic buffer, which provides a neutral pH. The pH of the neutralization reagent is preferably from about 7.0 to about 7.5, more preferably from about 7.1 to about 7.4.

Furthermore, the neutralization reagent can further comprise a serum albumin, such as bovine serum albumin. Serum albumin, particularly at a high concentration, can provide competitive binding of surfactant and inhibit action of surfactant on the cells. Therefore, serum albumin assists in preserving integrity of cellular components, particularly intracellular antigen sites, such as antigen sites of glycated hemoglobin (HbA1c) or fetal hemoglobin (HbF) for their binding with respective antibodies. Preferably, the concentration of serum albumin is from about 0.4 to about 1.2 mM. Moreover, the neutralization reagent further comprises an antimicrobial. In one exemplary embodiment, sodium azide is used. Sodium azide is a strong antimicrobial, which is particularly suitable for the neutralization reagent as it has a neutral pH and contains high concentration of bovine serum albumin. Example 1 illustrates an exemplary composition of the neutralization reagent.

Preferably, the neutralization reagent as shown in Example 1 is used with a ratio to the permeation reagent from about 0.3 to about 0.8. After addition of the neutralization reagent, the formed neutralization mixture is further incubated for a period time to effectively inhibit the reaction of the permeation reagent. This incubation time is preferably from about 5 minutes to about 30 minutes, and more preferably from about 8 minutes to about 12 minutes.

After neutralization, the treated blood cells, also referred to as permeated blood cells, or the formed cellular analogs, are stable and the cell mixture can be frozen for storage. However, the neutralization mixture contains salt, buffer, and bovine serum albumin, which may interfere with the assays to be performed subsequently. Therefore, the medium of the neutralization mixture is removed from the cellular analogs, and the cellular analogs are washed with a washing solution.

Preferably, a mild centrifugation is used to change the medium. As shown in Example 2, the neutralization mixture containing both the permeation and neutralization reagents is layered on a volume of a washing solution in a centrifuge tube. After centrifugation, the supernatant is removed. Then, a storage solution, also referred to as a suspension medium, is added to the packed cells to suspend the cellular analogs, which forms the reference control. Other suitable methods to change the medium can also be used, for example, filtration or dialysis.

It has been found that high speed centrifugation can have a deleterious effect on the analogs. If too high centrifugal forces are used, it can cause the analogs to stick together. Moreover, high speed centrifugation can cause the cells to lose parts of their cellular components. To prevent deleterious effects of centrifugation, a low speed centrifugation of the neutralization mixture over a layer of a washing solution is used. The washing solution contains one or more salts and has a neutral pH, and can contain a high concentration of sucrose. Preferably, the salt concentration is slightly higher than physiological salt concentration to inhibit aggregation of the cellular analogs.

It should be understood that the composition of the storage solution, which is the suspension medium of the analogs of the reference control, can be determined based on the assay to be performed subsequently. In other words, the composition of the suspension medium is compatible with the assay to be performed. Example 1 illustrates an exemplary storage solution composition suitable for cellular hemoglobin and hemoglobin variant measurement described herein. In this example, the storage solution is an aqueous solution containing a salt and a high concentration of sucrose and having a neutral pH.

It has been found that cellular hemoglobin of the red cell analogs can be determined using side scatter signals of the analogs measured on flow cytometric analyzers, as illustrated further in examples. This property of the red cell analogs of the present invention is substantially different from the property of untreated red blood cells in a whole blood, sphered red blood cells or stabilized red blood cells, since cellular hemoglobin of these cells are not able to be determined by side scatter measurement. Although the exact mechanism is not fully understood, it is believed that the direct correlation between the cellular hemoglobin of the red cell analogs and their side scatter signals is attributable to the property of aggregated hemoglobin in the permeated cells after treatment by the permeation reagent. The difference can be further appreciated by the fact that the red cell analogs obtained using the method of the present invention can not be lysed by a lytic reagent to release hemoglobin; while stabilized red blood cells, even after being treated with certain fixation conditions, can be lysed by lytic reagents to release hemoglobin for measurement on standard clinical chemistry analyzers by chromatography or immunoturbidimetry.

Furthermore, cellular membrane of the red cell analogs of the present invention have highly permeated, which allows macromolecular probes, such as antibodies to enter and to bind to intracellular proteins. It has been found that when the red cell analogs of the present invention are measured by impedance measurement, such as direct current (DC) impedance measurement on hematology analyzers, the impedance signals from these analogs are substantially smaller than those generated by untreated red blood cells or fixed red blood cells. DC impedance measurement has been commonly used on hematology analyzers for measuring the size of blood cells. The measurement is based on the increase of electrical resistance caused by a blood cell, which repels a volume of an electrical conductive solution being measured. As can be appreciated, since the cellular membrane of the instant red cell analogs are highly permeated, when the analogs are suspended in a conductive solution the conductive solution travels in and out the analogs freely, therefore, the impedance signals generated by these analogs are significantly reduced.

However, when being measured by forward light scatter measurement, which is also commonly used for measuring cell size, these permeated red blood cells exhibit substantially the same size of the sphered red blood cells. In this context, the red blood cell analogs are substantially different from fixed red blood cells. The latter are not permeable to antibodies and have substantially equivalent impedance signals as untreated red blood cells.

As described later, the permeation reagent and neutralization reagent used for making the cellular analogs for the reference control of the present invention are the same reagents used for processing the blood samples to be measured on the flow cytometric analyzers. The formed cellular analogs are washed and resuspended in the storage solution without being fixed by fixatives commonly used in making cellular analogs. However, as demonstrated subsequently by examples, in the absence of treatment by fixatives, these cellular analogs are stable when exposed to freezing and thawing conditions and maintain specificity of the antigen sites for immunoassays.

For long term stability, preferably, the reference control is kept frozen after being prepared. Typically, after preparation the reference control is dispensed into control vials. The control vials are then frozen and kept at a temperature typically not higher than $-10°$ C., preferably from $-10°$ C. to $-80°$ C. Preferably, the reference control is frozen in less than twenty four hours, more preferably, in less than two hours, most preferably within one hour after the preparation. During shipping to the customers, the reference control is kept frozen by dry ice, or other suitable materials. Prior to use, a vial of frozen reference control is thawed at room temperature. After thawing, the reference control is gently mixed to form a homogeneous analog suspension prior to being used.

As can be appreciated, for the purpose of the present invention the storage solution or suspension medium is suitable for storage under freeze and thaw conditions. In one embodiment, the storage solution is an aqueous solution comprising a salt and a saccharide. The salt concentration can be from about 0.05 M to about 2 M, preferably from about 0.1 M to about 0.5 M. The saccharide can be a polysaccharide, such as a disaccharide, or a monosaccharide. In an exemplary embodiment shown in Example 1, sucrose is used. The saccharide concentration can be from about 0.1 M to 2 M, preferably from about 0.5 M to about 1.5 M. It has been found that a relatively high concentration of saccharide, such as sucrose, prevents the cellular analogs from descending in the control vial after thawing the frozen analog suspension and during the use in the assay. Moreover, as described above, the suspension medium should also be compatible with the assay to be performed. For example, since phosphate tends to interfere with assays to be performed on the flow cytometric analyzers, whether to use a phosphate salt in the storage solution should be determined in consideration of the assay that the reference control is to be used for.

It has been found surprisingly that the cellular analogs of the reference control of the present invention are resistant to freezing and thawing treatment without using protective agents, and cellular antigenic sites and permeability of the cellular analogs to macromolecular probes, such as antibodies, are preserved after freezing and thawing of the analog suspension. Without being bound to any theory, it is believed that this unique property may be attributed to preservation of antigenic sites by the aggregated intracellular proteins. As described hereinafter in the method of using the reference control, the cellular analogs of the instant reference control maintain their specificities to antibodies. When being added into a blood sample, the cellular analogs of the instant reference control undergo the same antibody-antigen reaction that the blood sample experiences in an assay and substantially simulate the blood cells of the sample on the instrument.

In a further embodiment, the present invention provides a reference control comprising cellular analogs labeled with a fluorescent marker. The cellular analogs produced with such labeling are herein referred to as labeled analogs, and the reference control containing the labeled analogs is referred to as labeled reference control. The labeled analogs of the reference control can be identified and differentiated from the blood cells of a sample conveniently by fluorescence measurement, when the reference control is added into a blood sample to function as an internal control of an assay.

To produce the labeled reference control, the method of the present invention described above further comprises labeling the blood cells used for making the cellular analogs. In one embodiment, a fluorescence dye, carboxyfluorescein diacetate succinimidyl ester, is used to label cellular proteins of the blood cells. Various other fluorescent markers can also be used for labeling the cells.

It is known that carboxyfluorescein diacetate succinimidyl ester (CFDA-SE) is a lipophilic molecule and a non-fluorescent compound that diffuses passively into cells. Within the cells, esterases remove the acetyl moieties, and the remaining carboxyfluorescein succinimidyl ester (CFSE) is markedly fluorescent. CFSE binds covalently to proteins and is well retained within the cells. CFSE has an excitation wavelength at 488 nm and emission wavelength at 510-550 nm, which is suitable for use on flow cytometric analyzers that have the excitation wavelength at 488 nm and a detector at 525 nm.

Example 2 illustrates an example of preparing labeled red cell analogs using a whole blood with the method of the present invention described above. As shown, in preparing the labeled cellular analogs the blood cells are separated from the plasma first, and washed with an isotonic diluent, such as phosphate buffered saline, or other suitable diluents, before exposing the blood cells to the fluorescence dye. To label blood cells using CFDA-SE, the washed blood cells are incubated in an isotonic solution containing CFDA-SE for a period of time sufficient for the dye to penetrate the cellular membrane and to allow CFSE label the intracellular proteins. The incubation time can be from about 1 hour to about 5 hours, preferably, from about 2 hours to about 4 hours. After incubation, the labeled blood cells are washed with the isotonic diluent to remove excess dyes in the medium prior to exposing the labeled blood cells to the permeation reagent. The subsequent processing steps, i.e., reaction with the permeation reagent, inhibition with the neutralization reagent, washing, and freezing and thawing, are the same as described above in the process of preparing the reference control without labeling.

Preferably, prior to exposing to the permeation reagent, the labeled blood cells are resuspended in the autologus serum as described in Example 2, or other serum, to form a reconstituted blood. The presence of serum protects the blood cells from loss of hemoglobin during subsequent preparation steps. Preferably, the reconstituted blood is mixed with the permeation reagent with a reagent to blood ratio of about 100:1 or higher. Optionally, for measuring cellular hemoglobin the labeled red blood cells can be exposed to a sphering reagent to sphere the labeled red blood cells, prior to being treated with the permeation reagent.

In the method of measuring cellular hemoglobin and hemoglobin variant of mature red blood cells and reticulocytes as described hereinafter, the reticulocytes are differentiated from mature red blood cells by fluorescence measurement using a nucleic acid dye. The cellular analogs labeled with a fluorescence marker need to be differentiable from the reticulocytes stained with a nucleic acid dye. As illustrated in Example 3, the cellular analogs labeled by CFSE and the nucleic acid dye stained reticulocytes of the blood sample are both detected at 525 nm (FL1), however, the FL1 signals of CFSE are substantially stronger than the FL1 signals of acridin orange used for staining RNA of the reticulocytes. This intensity difference enables differentiation of the labeled analogs of the reference control from the mature red blood cells and the reticulocytes of the blood sample when the reference control is used as an internal control of the assay.

It is known that binding of a fluorescence marker to protein could potentially affect antigen sites of the protein or interfere with antibody binding. Therefore, it is important that the labeled analogs of the reference control substantially retain their binding specificity and affinity to antibodies used for the assay.

It has been found that after labeling with the fluorescence mark, the properties of the cellular analogs described above are maintained. More specifically, the cellular hemoglobin of the labeled cellular analogs can be measured using their side scatter signals as described above and as further demonstrated in the examples hereinafter. The specificity of antigenic sites of the proteins and permeability of the membrane are maintained. Moreover, the resistance of the labeled analogs to freezing and thawing treatment is also maintained. The reference control of the present invention, containing either labeled cellular analogs or unlabeled analogs, can be stored under freezing condition described above for at least more than one year while maintaining the properties of the cellular components of the cellular analogs.

Example 2 illustrates making a labeled reference control from a normal human whole blood. Example 4 further illustrates a labeled reference control made from a whole blood of a diabetic patient, and the stability of the labeled reference control after thawing in the measurements of cellular hemoglobin using side scatter measurement and HbA1c using fluorescence measurement, which is further described in more detail hereinafter.

The cellular hemoglobin, specific hemoglobin variant content such as HbA1c, and percentage of a specific hemoglobin variant of the reference control can be determined using side scatter and fluorescence measurements on a flow cytometric analyzer, which are further described in detail hereinafter. The term "flow cytometric analyzer" refers to flow cytometers known in the art and hematology analyzers that are equipped with light scatter and/or fluorescence detection devices. The reference values of these parameters of the reference control can be assigned by measuring blood samples that have known values of these parameters obtained from existing reference methods and the reference control on the same flow cytometric analyzer under the same operating conditions. Various reference methods are known in the art, for example, the mean cellular hemoglobin content (MCH) of a blood sample can be obtained from hematology analyzers, and HbAc1 percentage can be obtained using affinity chromatography, immunoturbidimetry, or ionic-exchange chromatography. Example 7 illustrates a detailed process of assigning reference values for the reference control of the present invention.

In a further aspect, the present invention provides a method of using the reference control described above for cell by cell analysis of cellular components of cells on flow cytometric analyzers. The reference control can be used either as a stand-alone control or an internal control. The term of stand-alone control refers to a reference control to be analyzed alone on a flow cytometric analyzer, without mixing with a sample. The stand-alone control is typically analyzed with a batch of samples as a reference for intra or inter assay purposes. The term of internal control refers to a reference control being added into a sample and analyzed together with the sample on a flow cytometric analyzer.

The method of using the instant reference control for cell by cell analysis is illustrated hereinafter with the example of measurement of cellular hemoglobin and cellular percentage of hemoglobin variants. It should be understood, however, that the reference control made using the method of the present invention can also be used for measurement of other cellular constituents.

Herein, the term "cellular hemoglobin" refers to the total hemoglobin content in an individual red blood cell, which includes all hemoglobin variants present in that cell. The term of cellular hemoglobin of reticulocytes refers to the total hemoglobin content in an individual reticulocyte, which includes all hemoglobin variants present in that reticulocyte. Cellular hemoglobin is also commonly referred to as cell-by-cell hemoglobin. The term "hemoglobin variant" refers to all hemoglobin variants, for example fetal hemoglobin, glycated hemoglobin such as HbA1c, and aberrant forms of hemoglobin, such as those found in sickle cell disease and thalassemia. The term "cellular hemoglobin variant" is the amount of a hemoglobin variant in an individual red blood cell. The term "cellular percentage of a hemoglobin variant" refers to the percentage of a hemoglobin variant vs. the total hemoglobin content in an individual red blood cell. For example, in the measurement of HbA1c described herein it is expressed as cellular percentage of HbA1c, or cellular HbA1c percentage. Therefore, the percentage of a hemoglobin variant of a sample obtained using the method of the present invention is the mean or average of cellular percentage of this hemoglobin variant of all measured red blood cells of a blood sample.

To use the instant reference control for cellular hemoglobin and cellular hemoglobin variant measurements of a blood sample on a flow cytometric analyzer, a reference control containing red cell analogs made of permeated red blood cells is provided. The red cell analogs comprise therein aggregated intracellular proteins and preserved antigenic sites of the hemoglobin variant of interest, and have cellular membrane permeable to antibodies. When it is used either as an internal control or a stand-alone control, the reference control is exposed to the same reagents and same assay procedure that a blood sample is exposed to (see Example 3), then analyzed on a flow cytometer by side scatter and fluorescence measurements. The cellular hemoglobin of the red blood cells of the blood sample and the red cell analogs of the reference control is determined using the side scatter signals; and the cellular hemoglobin variant of the red blood cells of the blood sample and the red cell analogs of the reference control is determined using fluorescence signals.

The method of measuring cellular hemoglobin and cellular hemoglobin variant of blood samples using side scatter and fluorescence measurements has been described in detail in U.S. 2007/0020612 A1, which is hereby incorporated by reference in its entirety.

More specifically, using this method a blood sample is mixed with a permeation reagent, which forms a first sample mixture. The first sample mixture is incubated for a period time sufficient to cause intracellular protein aggregation and to render the cellular membrane permeable to antibodies. Subsequently, a neutralization reagent is added into the first sample mixture to inhibit further reaction of the permeation reagent with the red blood cells, which forms a second sample mixture. Then, a side scatter measurement of the second sample mixture is performed on a flow cytometer. The cellular hemoglobin of the blood sample is determined using the side scatter signals obtained.

When a hemoglobin variant is measured, the neutralization reagent further contains a fluorescently labeled antibody specific to the hemoglobin variant of interest, such as anti-HbA1c or anti-Hbf antibody. As the cell membrane is permeated by the permeation reagent, the large antibody molecule can penetrate through the cellular membrane and bind to the antigen sites of the hemoglobin variant inside the red blood cells. The second sample mixture is incubated for a period of time to allow antibody binding. Then, a fluorescence measurement of the second sample mixture is performed simultaneously with the side scatter measurement, and cellular percentage of the hemoglobin variant can be determined using the fluorescence signals and the side scatter signals.

Moreover, when cellular hemoglobin and a hemoglobin variant of the reticulocytes of a blood sample are to be measured, the method further comprises staining the blood sample with a nucleic dye prior to exposing the blood sample with the permeation reagent as described above. Optionally, the nucleic dye can be included in a sphering reagent, which can enhance the speed of penetration of the nucleic dye into the cellular membrane.

In a semi-automated measurement process, the second sample mixtures described above are measured on a flow cytometer in a batch by batch manner. The prepared sample mixtures may wait for a substantial period of time before the measurement is made, for example, a couple of hours. Therefore, in the instant method, a fixation reagent can be optionally added to the second sample mixture to fix the cells.

The fixation reagent comprises a fixative, an osmolality adjusting agent and a buffer. Preferably, the fixative is an aldehyde, including, but not limited to, formaldehyde, paraformaldehyde, or glutaraldehyde. The osmolality adjusting agent can be one or more alkaline metal salt, preferably alkaline metal halides, such as sodium or potassium chloride. Preferably, the fixation reagent is hypertonic, with an osmolality from about 1,100 to about 1,400 mOsm/kg $H_2O$. The buffer can be an organic or inorganic buffer, which provides a neutral pH. The pH of the fixation reagent is preferably from about 6.9 to about 7.3, which maintains the neutral pH achieved by the neutralization reagent. Furthermore, preferably the fixation reagent further comprises chelating agents such as dextran sulfate, EGTA, and boric acid. It has been found that the combination of dextran sulfate, EGTA and boric acid in the fixation reagent can effectively prevents cell aggregation in the final sample mixture, in comparison to the commonly used fixing reagent containing formaldehyde and phosphate buffered saline. Example 1 shows an exemplary composition of the fixation reagent.

Example 3 illustrates a process of measuring cellular hemoglobin and hemoglobin variant of a blood sample using a labeled reference control, made from a normal whole blood using the method of Example 2, as an internal control. As described in Example 3, a volume of a whole blood sample was first mixed with a sphering reagent containing acridin orange to stain RNA of the reticulocytes. Then, a volume of the stained sample mixture was mixed with the permeation reagent of Example 1, forming the first sample mixture. After incubation, the labeled reference control was added into the first sample mixture. Subsequently, the neutralization reagent of Example 1 containing a fluorescent anti-$Hb_{A1c}$ antibody was added, forming a second sample mixture. The second sample mixture was incubated to allow the antibody penetrating the permeated cellular membrane and binding to HbA1c antigens. Then the fixation reagent of Example 1 was added, forming a final sample mixture.

The final sample mixture was analyzed on a Beckman Coulter FC500 MCL cytometer by forward scatter and side scatter measurements and fluorescence measurements at 525 nm (FL1) and at 675 nm (FL4). FIGS. 1A to 1C showed the obtained scattergrams of forward scatter (FS) vs. side scatter (SS), FS vs. FL1 and FL1 vs. FL4, respectively.

Herein, the term of side scatter signal, as known in flow cytometry, refers to the light scatter signal at about 90° or at the right angle from the incident light, generated by a particle or a blood cell passing through an aperture of a flow cell. The forward scatter signal refers to the light scatter signal measured less than 10° from the incident light. The term of side scatter measurement refers to the measurement of the side scatter signals by an optical detector. Most commercially available flow cytometers are equipped with a detection system which enables measurement of the forward scatter and side scatter signals.

In FIG. 1A, region A contained the red blood cells of the blood sample and the analogs of the labeled reference control, which were gated on this scattergram for further differential analysis using fluorescence as shown in FIGS. 1B and 1C. The populations outside region A were white blood cells and platelets.

In FIG. 1B, region B contained the mature red blood cells of the blood sample; region C contained reticulocytes of the blood sample which were stained with acridin orange; and region D contained the analogs of the labeled reference control, which were labeled with CFSE. As shown, the mature red blood cells and reticulocytes of the blood sample and the analogs of the labeled reference control are differentiated one from another in FL1 axis.

In FIG. 1C, region F contained the mature red cells of the blood sample, region G contained the reticulocytes of the blood sample, and region E contained the analogs of the labeled reference control.

As can be appreciated, the fluorescence measurement at 525 nm (FL1) measures fluorescence signals generated from both acridin orange stained RNA and CFSE labeled intracellular proteins. As described above, acridin orange is used to differentiate reticulocytes from mature red blood cells, and CFSE is used to label the cellular analogs of the reference control. Although both signals can be detected at the same wavelength, the CFSE labeled cellular analogs have substantially stronger signals than the reticulocytes. Therefore, the analogs of the reference control do not overlap with the reticulocytes on FL1 axis of the scattergrams, and can be differentiated from the reticulocytes.

The mean cellular hemoglobin of the blood sample was obtained from the mean of the side scatter values of individual red blood cells of the blood sample. The HbA1c content of the blood sample was obtained from the mean of the fluorescence signals at 675 nm (FL4), after subtraction of a fluorescence background value. The percentage of HbA1c of the blood sample was calculated by dividing the HbA1c content of the blood sample by the mean cellular hemoglobin of the blood sample. Since mature red blood cells and reticulocytes are differentiated from each other, mean cellular hemoglobin and percentage of HbA1c can be obtained for each of these two red blood cell subpopulations of the blood sample.

Similarly, since the red cell analogs of the labeled reference control are differentiated from both mature red blood cells and reticulocytes of the blood sample, the mean cellular hemoglobin and percentage of HbA1c can be obtained for the reference control using the side scatter signals and fluorescence signals from the red cell analogs using the same calculations described above.

As can be appreciated, when blood samples having known values of mean corpuscular hemoglobin (MCH, which is the total hemoglobin) and percentage of HbA1c obtained from existing reference methods are measured together with the reference control using the instant method, these known values and the mean of the side scatter signals and the mean of the fluorescence signals of the blood samples can be used to assign reference values of these parameters to the reference control of the present invention, as illustrated in Example 7.

When the reference control having assigned reference values are used as an internal control in the blood samples to be tested, mean cellular hemoglobin and percentage of HbA1c of the blood samples can be obtained using the reference control. Examples 7 and 8 illustrate such an exemplary process. It is noted that the same mechanism also applies when the reference control is used as a stand-alone control. Furthermore, in Examples 7 and 8 the processes of obtaining mean cellular hemoglobin and percentage of HbA1c of the blood samples using the reference control of the present invention have been described in detail in order to compare with the results generated by the standard methods from the reference laboratory, which are one value for each parameter, i.e., total hemoglobin and percentage of HbA1c, obtained from the hemolysate of each sample tested. However, other than the means of cellular hemoglobin and cellular percentage of HbA1c, more importantly, the method of the present invention provides cellular hemoglobin and cellular percentage of HbA1c of individual red blood cells.

It has been found that the stability of the instant reference control after thawing is equivalent to fresh blood in terms of intracellular protein content and intracellular antigens. Example 4 illustrates such an example. As shown, a labeled reference control was prepared using a whole blood from a diabetic patient with the preparation process described above. In the stability tests, the labeled reference control was added into a normal blood sample as an internal control, and then the blood sample was measured using the assay procedure described in Example 3.

Assays were performed immediately after thawing of a vial of frozen analog suspension, at 1.5 hours, 2.5 hours, and 20 hours after thawing, respectively. During the tests, the blood sample and the labeled reference control were both kept at room temperature before adding the labeled reference control into the blood sample. The analyses of the side scatter signals and FL4 signals of the red blood cells of the blood sample and the red cell analogs of the labeled reference control were performed separately. More specifically, the mature red blood cells and reticulocytes of the blood sample and the red cell analogs of the reference control were first differentiated on the FS vs. FL1 scattergrams as illustrated in FIG. 1B. After differentiation, side scatter signals for each of these populations were obtained. The FL4 signals of the mature red blood cells, reticulocytes, and the red cell analogs were obtained from FL1 vs. FL4 scattergrams as illustrated in FIG. 1C.

Figure 2B:
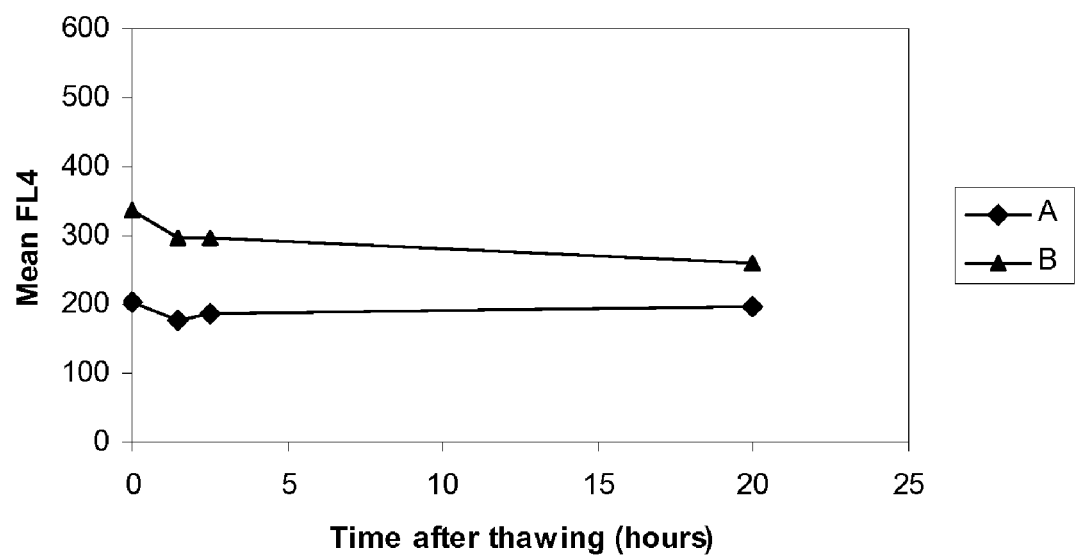

FIGS. 2A and 2B show the mean side scatter signals and mean FL4 signals versus the time after thawing of the labeled reference control, respectively. As shown, the mean side scatter signals of the red blood cells of the blood sample and the red cell analogs of the labeled reference control were stable within 20 hours, indicating stable hemoglobin content of the red cell analogs after thawing. Since hemoglobin constituted 99% of the red blood cell dry mass, this result indicated that no loss of cellular components occurred after the thawing of the labeled cellular analogs.

On the other hand, a small decrease of the FL4 signals was observed in the first two hours after thawing, indicating a small decrease of the amount of HbA1c antigen in both the red blood cells of the blood sample and the red cell analogs of the reference control. However, after the initial decrease, FL4 signals of the red cell analogs were stable within 20 hours. As shown, the FL4 signals of the red cell analogs were slightly more stable than the red blood cells of the blood sample.

Although Example 4 illustrates the stability of the instant reference control in measurement of cellular hemoglobin and hemoglobin variant, the reference control of the present invention containing the frozen and thawed cellular analogs can be used for flow cytometric assay of other cellular components. The reference control can be used to homogenize the data from different samples within an assay (intra assay) as well as data from assays that are run separately in place or time (inter assay).

Example 5 illustrates the effectiveness of using the reference control of the present invention in correcting inter assay variations in a simulated situation. A labeled reference control made from a diabetic patient was used as the internal control. A blood sample was prepared using the assay procedure described in Example 3 and analyzed on a FC500 MCL cytometer at different voltages of the photomultiplier tube (PMT) of the FL4 detector. The side scatter signals and the FL4 signals of the mature red blood cells and the red cell analogs were obtained at each PMT setting. At each PMT setting, the HbA1c percentage of the red blood cells of the blood sample was obtained by dividing the mean FL4 value by the mean side scatter value of the red blood cells. Similarly, the HbA1c percentage of the red cell analogs of the labeled reference control was obtained by dividing the mean FL4 value by the mean side scatter value of the analogs at each PMT setting.

Figure 3:
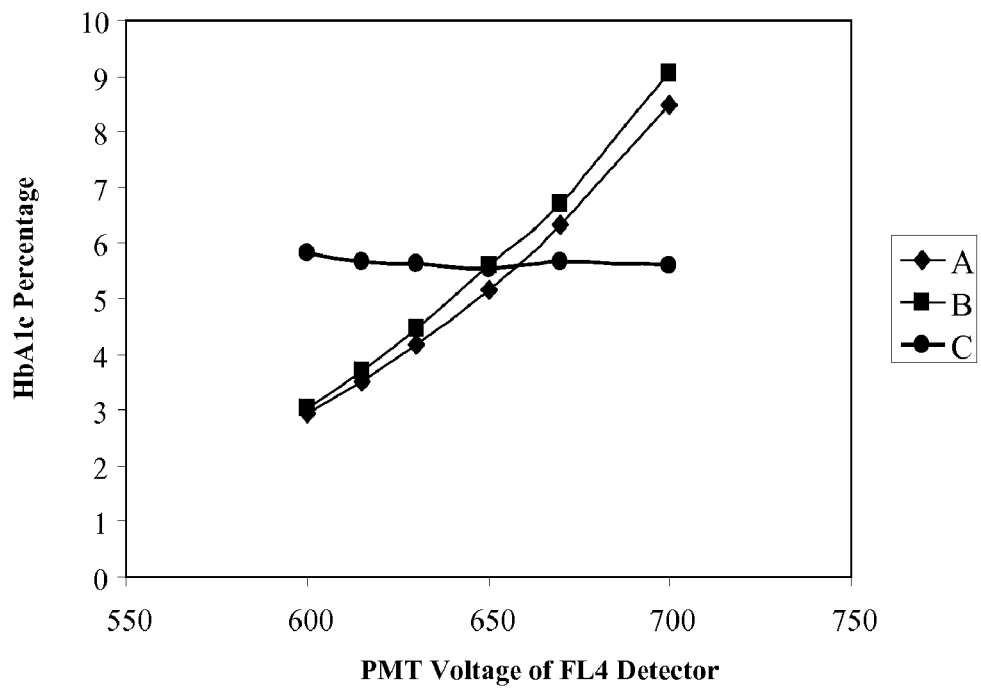
FIG. 3 shows the change of HbA1c percentage with the change of the voltage of PMT used for measurement of FL4 signals, and the corrective effect achieved using the instant reference control.

FIG. 3 showed the HbA1c percentages of the mature red blood cells of the blood sample and the red cell analogs of the reference control at different PMT settings. As shown, the increase of PMT voltage increased the HbA1c percentage of the blood sample (curve A) and the control (curve B). However, after dividing the HbA1c percentage of the blood sample by the HbA1c percentage of the reference control at each PMT setting and normalization, the obtained corrected HbA1c percentages of the blood sample (curve C) at different PMT settings were constant and reproducible.

The variation of PMT voltage used in this example simulates fluorescence signal variation caused by the instrument. Since the reference control experiences the same changes that the blood sample experiences, the effects of the changes on the apparent value of the measurement can be eliminated using the reference control. This example demonstrates that the reference control of the present invention can be used to homogenize data and correct inter assay variations caused by external factors such as instrument, temperature or assay reagents.

Example 6 illustrates the effectiveness of using the reference control of the present invention in correcting intra assay variations in a simulated situation. A series of test samples were prepared from a whole blood sample, and each of the test samples has a different red blood cell concentration. The test samples were processed and analyzed according to the assay procedure described in Example 3, with the labeled reference control made from a diabetic patient as the internal control.

Figure 4:
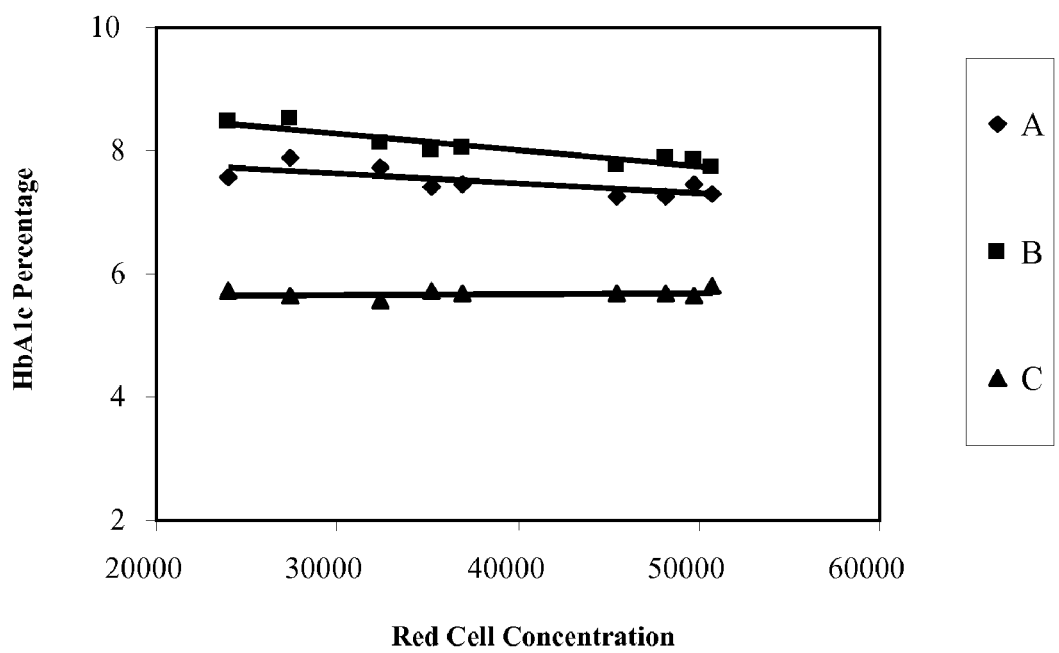
FIG. 4 shows the change of HbA1c percentage with the change of the red blood cell concentration of a reconstituted blood sample and the corrective effect achieved using the instant reference control.

FIG. 4 showed the HbA1c percentages of the red blood cells of the test samples and the red cell analogs of the reference control versus the red blood cell concentrations of the test samples. As shown, the HbA1c percentages of the test samples (curve A) and the reference control (curve B)

decreased with the increase of the red blood cell concentration of the test samples. However, after dividing the HbA1c percentage of the test samples by the HbA1c percentage of the reference control and normalization, the obtained corrected HbA1c percentages of the test samples (curve C) with different red blood cell concentrations were substantially equivalent, which were independent of the blood cell concentration change.

As can be understood, when used as an internal control, the cellular analogs of the reference control are exposed to the same condition that the blood sample experiences. Hence, the effects of the changes on the apparent value of the measurement can be eliminated using the reference control. This example further demonstrates that the reference control of the present invention can be used to correct intra assay variations caused by intrinsic factors of blood samples.

Examples 7 and 8 further illustrate the corrective effects of the instant reference control on inter and intra assay variations. In Example 7, a detailed process is provided on assigning reference value of HbA1c percentage to the labeled reference control using a first series of 20 blood samples having known HbA1c percentages obtained from three existing reference methods reported by a reference laboratory. After assigning the reference value to the reference control, HbA1c percentages of other two series of blood samples were determined using the labeled reference control as an internal control. For the purpose of comparison, the HbA1c percentages of other two series of blood samples were also calculated using the first series of blood samples as the reference, without using the information from the instant reference control.

As shown in Tables 3 and 4, the mean of HbA1c percentages of the three series of blood samples obtained using the instant reference control correlated substantially better than those obtained without using the reference control. Moreover, the standard deviation of the results of the three series with the internal control was 0.015, which is substantially improved from a standard deviation of 0.079 without the internal control.

In the assessment of the corrective effect of intra assay variation in Example 8, the results show that the HbA1c percentages of the blood samples obtained using the instant method with the labeled reference control as an internal control correlate with the results from the existing reference methods substantially better than those obtained without using the internal control. Therefore, using the instant reference control improves intra assay consistency.

The reference control of the present invention has several advantages. First, the cellular analogs of the reference control have permeated cellular membrane that is permeable to macromolecular probes, such as fluorescence labeled antibodies commonly used for immunoassay, and can be used for cell by cell assays which use intracellular markers for labeling intracellular components to simulate intracellular marker binding process of a sample to be measured. Second, the cellular hemoglobin of the cellular analogs of the reference control can be measured using a simple side scatter measurement. This provides a strong advantage of measuring the total hemoglobin of each cell and a hemoglobin variant of the cell in one single step measurements of side scatter and fluorescence signals. Both measurements are available on most of commercial flow cytometers. Third, the cellular analogs of the reference control are labeled with a fluorescence marker. Therefore, the reference control can be used as an internal control. The cellular analogs can be easily identified and differentiated from the blood cells of the samples to be measured. Fourth, the reference control is resistant to freeze-thaw treatment without degradation of the cellular components of the cellular analogs to be measured, and maintaining permeability of the cellular membrane after freezing and thawing. As such, the reference control of the present invention can be stored for substantially longer time than the stabilized cells known in the art, which means substantially longer product stability. As described above, the reference control of the present invention can be stored under freezing condition described above for at least more than one year while maintaining the properties of the cellular components of the cellular analogs. Fifth, as further described above, in the process of preparing the reference control, no traditional protective agents, such as glycerol or dimethylsulfoxide, are used. Therefore, it avoids interference of these chemicals to the assay to be performed, particularly when the reference control is added into a sample and used as an internal control. In view of the above described advantages, the reference control of the present invention has provided significant improvements in utility and stability of reference controls in flow cytometry.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Reagents Used for Preparing the Cellular Analogs for Measurement of Cellular Hgb on Flow Cytometer Sphering Reagent Composition An aqueous sphering reagent was prepared according to the following composition:

| Component | Concentration |
| --- | --- |
| Sodium chloride | 137 mM |
| HEPES | 5 mM |
| D(+) Trehalose | 0.5 mM |
| Formaldehyde | 83 mM |
| n-Dodecyl beta-D-maltoside | 40 mM |
| Proclin ®-300 | 0.5 ml/l |
| Sodium hydroxide | quantity to adjust pH at 7.5 |
| Deionized water | q.s. to 1 liter |

It is noted that all reagents described herein were filtered through a sterile nylon filter of 0.22 µm pore size, unless stated otherwise.

Permeation Reagent Composition

Following permeation reagent was prepared according to the following composition:

| Component | Concentration |
| --- | --- |
| N-lauroyl sarcosine | 2.03 mM |
| Succinic acid | 10 mM |
| Sucrose | 0.22 M |
| Bovine serum albumin | 0.015 mM |
| Proclin 300 | 0.5 ml/l |
| Pyrrolidine | quantity to adjust pH at 5.4 |
| Deionized water | q.s. to 1 liter |

The reagent had a conductivity of 0.99 mS/cm and osmolality of 268 mOsm/Kg $H_2O$. Proclin 300 was obtained from Zymed laboratories, South San Francisco, Calif.

Neutralization Reagent Composition

An aqueous neutralization reagent was prepared according to the following composition:

| Component | Concentration |
|---|---|
| HEPES | 40 mM |
| Sodium chloride | 0.5 M |
| Bovine serum albumin | 0.91 mM |
| Sodium azide | 0.03 M |
| Sodium hydroxide | quantity to adjust pH at 7.25 |
| Deionized water | q.s. to 1 liter |

Washing Solution Composition

A washing solution was prepared according to the following composition:

| Component | Concentration |
|---|---|
| Sodium chloride | 0.3 M |
| Sucrose | 0.58 M |
| Deionized water | q.s. to 1 liter |
| pH between 5 and 8 | |

Storage Solution Composition

A storage solution was prepared according to the following composition:

| Component | Concentration |
|---|---|
| Sodium chloride | 0.3 M |
| Sucrose | 0.87 M |
| Deionized water | q.s. to 1 liter |
| pH between 5 and 8 | |

Fixation Reagent Composition

An aqueous fixation reagent was prepared according to the following composition:

| Component | Concentration |
|---|---|
| Sodium chloride | 155 mM |
| Disodium hydrogen phosphate dihydrate | 40 mM |
| Formaldehyde | 0.62 M |
| Boric acid | 180 mM |
| EGTA | 10 mM |
| Dextrane sulfate (MW 500.000) | 0.016 µM |
| Sodium hydroxide | quantity to adjust pH at 7.1 |
| Deionized water | q.s. to 1 liter |

Fluorescent Anti-HbA1c Antibody

The fluorescent anti-$Hb_{A1c}$ antibody was prepared by covalently binding a fluorescent dye molecule, Alexa Fluor 647, to the monoclonal anti-$Hb_{A1c}$ antibody at a molecular ratio of five dye molecules per antibody molecules, according to the manufacturer's instructions. Alexa Fluor 647 was manufactured by Invitrogen Corporation, Carlsbad, Calif. The dye had a maximum absorption at 647 nm.

EXAMPLE 2

Preparation of a Labeled Reference Control

A whole blood was collected from a donor, with 0.7 mM ethylenediamine tetraacetic acid (EDTA) as anticoagulant. The whole blood was stored at 4° C. for no more than three days.

Autologous serum was prepared from a portion of the whole blood. The whole blood was centrifuged at 300 g for 5 minutes and the supernatant was depleted of particles by a second centrifugation of 5 minutes at 13,000 g.

0.1 ml of the whole blood was washed three times with 1 ml of phosphate buffered saline (PBS) by centrifugation at 300 g. After washing, 1 ml of PBS mixed with 0.01 ml of carboxyfluorescein diacetate succimidyl ester (CFDA-SE) was added to the pellet, and the cell suspension was incubated for three hours at room temperature with occasionally mixing to allow carboxy fluorescein succimidyl ester (CFSE) to label cellular proteins. After incubation, the cell suspension was centrifuged at 300 g and washed one more time with 1 ml of PBS. The pellet was taken up in 0.05 ml of autologous serum to form a reconstituted and labeled blood. The PBS used contained 150 mM sodium chloride and 10 mM sodium phosphate, having a pH of 7.4. The carboxyfluorescein diacetate succimidyl ester had a concentration of 10 mg/ml in dimethyl sulfoxide, which was stored at −20° C. prior to use.

The reconstituted and labeled blood was mixed with 0.4 ml of the sphering reagent of Example 1 and incubated for 2 minutes at room temperature. After the incubation, 16 ml of the permeation reagent of Example 1 was added, mixed and incubated for an additional 3 minutes at room temperature to permeate cellular membrane and cause intracellular protein aggregation. Then, 8 ml of the neutralization reagent of Example 1 was added to inhibit further reaction of the permeation reagent. The formed neutralization mixture, having a total volume of 24.45 ml was layered on 20 ml of the washing solution of Example 1 in a centrifuge tube and was centrifuged for 10 minutes at 300 g. After removing the supernatant, the pellet was taken up in 5 ml of the storage solution of Example 1 to form an analog suspension, which is the labeled reference control. The analog suspension was dispensed at a volume of 0.5 ml into 1 ml vials, closed and frozen at −50° C. in less than one hour. Prior to use, a vial of frozen labeled reference control was thawed at room temperature and gently mixed to form a homogeneous analog suspension prior to being added into a blood sample to be tested, or use as a stand-alone control.

EXAMPLE 3

Assay Measuring Cellular Hemoglobin and Percentage of Glycated Hemoglobin (HbA1c) of a Blood Sample Using the Labeled Reference Control as an Internal Control A whole blood sample collected in a test tube containing 0.7 mM EDTA as the anticoagulant was used. The blood sample was stored at 4° C. for not more than three days. A labeled reference control prepared using a whole blood from a diabetic patient and the preparation process of Example 2 was used for the assay.

An aliquot of 4 µl of the whole blood sample was mixed with 200 µl of the sphering reagent of Example 1, which further contained 8.3 µM of acridin orange, and formed a stained sample mixture. After 1 minute of incubation, 3 µl of the stained sample mixture was mixed with 60 µl of the permeation reagent of Example 1, forming a first sample mixture. After 1.5 minutes of incubation, 5 µl of the labeled reference control was added into the first sample mixture and mixed. After 1 minute of incubation, 100 µl of the neutralization reagent of Example 1 was added and mixed, forming a second sample mixture. The neutralization reagent contained 5 mg/l of fluorescent anti-Hb$_{A1c}$ antibody of Example 1. After another 10 minutes of incubation, 80 µl of the fixation reagent of Example 1 was added, forming a final sample mixture.

The final sample mixture was analyzed on a FC500 MCL cytometer by forward scatter and side scatter measurements and fluorescence measurements at 525 nm (FL1) and at 675 nm (FL4). FIGS. 1A to 1C showed the obtained scattergrams of forward scatter (FS) vs. side scatter (SS), FS vs. FL1 and FL1 vs. FL4, respectively.

In FIG. 1A, region A contained the red blood cells of the blood sample and the red cell analogs of the labeled reference control, which were gated on this scattergram for further differential analysis using fluorescence as shown in FIGS. 1B and 1C. The populations outside region A were white blood cells and platelets. In FIG. 1B, region B contained the mature red blood cells of the blood sample; region C contained reticulocytes of the blood sample which were stained with acridin orange; and region D contained the red cell analogs of the labeled reference control, which were labeled with CFSE. In FIG. 1C, region F contained the mature red blood cells of the blood sample, region G contained the reticulocytes of the blood sample, and region E contained the red cell analogs of the labeled reference control.

The mean cellular hemoglobin of the sample (which correlates to MCH) was obtained from the mean of the side scatter values (SS) of individual red blood cells measured by the FC500 MCL cytometer. The HbA1c content of the blood sample was obtained from the mean of the fluorescence signals of the individual red blood cells at 675 nm (FL4), after subtraction of a fluorescence background value. The fluorescence background value was obtained by analyzing blood samples using the assay procedure described above, in the absence of the HbA1c antibody and in the presence of a non-specific isotypic control monoclonal antibody (IgG1) which was covalently conjugated to Fluor Alexa 647. The HbA1c percentage of the blood sample was obtained from the mean of FL4/SS values from all measured red blood cells of a blood sample, which is a mean or average of cellular HbA1c percentage of the red blood cells.

EXAMPLE 4

Stability of the Reference Control after Thawing

A labeled reference control was prepared using a whole blood from a diabetic patient and with the preparation process described in Example 2. This labeled reference control was added into a normal whole blood sample, as an internal control, and the blood sample was analyzed using the assay procedure described in Example 3.

Assays were performed immediately after thawing of a vial of frozen analog suspension, at 1.5 hours, 2.5 hours, and 20 hours after thawing, respectively. In the time intervals among the assays, the blood sample and the labeled reference control were both kept at room temperature before adding the labeled reference control into the blood sample. The settings of the cytometer were unchanged during this experiment.

The analysis of the side scatter and FL4 signals of the red blood cells of the blood sample and the analogs of the reference control were performed separately. More specifically, the mature red blood cells and reticulocytes of the blood sample and the red cell analogs of the reference control were first differentiated on the FS vs. FL1 scattergrams as illustrated in FIG. 1B. After differentiation, side scatter signals for each of these populations were obtained. The FL4 signals of the mature red blood cells, reticulocytes, and the analogs were obtained from FL1 vs. FL4 scattergrams as illustrated in FIG. 1C.

FIGS. 2A and 2B showed the mean side scatter signals and mean FL4 signals versus the time after thawing of the labeled reference control, respectively. The curves designated by A were obtained from the red blood cells of the blood sample and the curves designated by B were obtained from the red cell analogs of the labeled reference control. In FIGS. 2A and 2B, time zero is the time when thawing was complete.

As shown, the mean side scatter signals of the red blood cells of the sample and the red cell analogs of the labeled reference control were stable within 20 hours, indicating stable hemoglobin content of the analogs after thawing. On the other hand, a small decrease of the FL4 signals was observed in the first two hours after thawing, indicating a small decrease of the amount of HbA1c antigen in both the red blood cells of the blood sample and the analogs of the reference control. However, after the initial decrease, FL4 signals of the red cell analogs were stable within 20 hours. As shown, the FL4 signals of the analogs were slightly more stable than the red blood cells of the blood sample.

EXAMPLE 5

Use of the Reference Control in Simulating Inter Assay Variation by the Change of FL4 Detector Voltage A normal whole blood sample was used in this experiment, with the labeled reference control made from a diabetic patient as the internal control.

The blood sample was prepared using the assay procedure described in Example 3 and analyzed on a FC500 MCL cytometer at different voltages of the photomultiplier tube (PMT) of the FL4 detector. The side scatter and the FL4 signals of the mature red blood cells and the red cell analogs were obtained at each PMT setting, with the process described previously. At each PMT setting, the HbA1c percentage of the red blood cells of the blood sample was obtained by dividing the mean FL4 value by the mean side scatter value of the red blood cells. Similarly, the HbA1c percentage of the analogs of the labeled reference control was obtained by dividing the mean FL4 value by the mean side scatter value of the analogs at each PMT setting.

FIG. 3 showed the HbA1c percentages of the mature red blood cells of the blood sample and the red cell analogs of the control at different PMT settings. As shown, the increase of PMT voltage increased the HbA1c percentage of the blood sample (curve A) and the control (curve B). However, after dividing the HbA1c percentage of the blood sample by the HbA1c percentage of the reference control at each PMT setting, and multiplied by a factor of 6 to normalize the data, the obtained corrected HbA1c percentages of the blood sample (curve C) at different PMT settings were constant and reproducible.

EXAMPLE 6

Use of the Labeled Reference Control in Simulating Intra Assay Variation by Changing the Red Cell Concentration in a Sample Test samples having different concentrations of red blood cells were prepared as followings. A whole blood sample with EDTA as the anticoagulant (see Example 2) was centrifuged at 300 g. The serum was removed, and then the packed cells were resuspended in an amount of the serum, about one third of the volume of the packed cells. 100 μl of the resuspended cells were distributed into each of nine tubes, and to each tube a different volume of the serum was added, varying from zero to 160 μl. The actual concentrations of red blood cells of these test samples were determined by counting the cells in the cytometer.

The test samples were processed and analyzed according to the assay procedure described in Example 3, with the labeled reference control made from a whole blood of a diabetic patient as the internal control.

FIG. 4 showed the HbA1c percentages of the red blood cells of the test samples and the red cell analogs of the reference control versus the red blood cell concentrations of the test sample. As shown, the HbA1c percentages of the test samples (curve A) and the reference control (curve B) decreased with the increase of the red blood cell concentration of the test samples. However, after dividing the HbA1c percentage of the test samples by the HbA1c percentage of the reference control, and multiplied by a factor of 6 to normalize the data, the obtained corrected HbA1c percentages of the test samples (curve C) with different red blood cell concentrations were substantially equivalent.

EXAMPLE 7

Correction of Inter Assay Variation in Measurement of the Percentage of HbA1c Using the Reference Control Three series of 20 blood samples were used for assessing inter assay variation in measurement of percentage of HbA1c using the labeled reference control as the internal control. The HbA1c percentage of each blood sample was determined by a reference laboratory using three different HbA1c measurement standard methods, more specifically, using affinity chromatography on Primus Ultra2 (Primus Diagnostics, Missouri), immunoturbidimetry on Roche Unimate (Roche Diagnostic Corporation, Indiana), and ionic-exchange chromatography on Tosoh G7 variant (Tosoh Bioscience Inc., California). The HbA1c percentages of the reference laboratory were according to the NGSP standardization (David Sachs for the ADA/EASD/IDF working group of the HbA1c assay; Clinical Chemistry 2005; 51: 681-683). Between the first and the second series there was a time interval of 4 weeks, and between the second and the third series there was a time interval of 2 weeks.

In parallel with the HbA1c measurements performed by the reference laboratory, the 20 blood samples of each series were analyzed using the method of the present invention with the assay procedure described in Example 3, using the labeled reference control made from a whole blood of a diabetic patient as the internal control. The experimental conditions and cytometer settings remained the same in the analyses of all three series of blood samples.

The HbA1c percentages obtained using the instant method were calculated from the raw data collected on a FC500 MCL cytometer as follows:

1. A fraction of 13.3% of the FL1 signals generated by acridin orange and/or CFSE was subtracted from the FL4 signals of anti-Hb$_{A1c}$-Alexa Fluor 647 antibody to compensate for the spill over of FL1 into FL4. This is a FL1-FL4 compensation, commonly used in multi-color fluorescence measurement on flow cytometers.

2. A fluorescence background value, obtained as described in Example 3, was subtracted from the resulted FL4 values.

3. The corrected FL4 value of a red blood cell obtained after steps 1 and 2, which represented cellular HbA1c content of the red blood cell, was divided by the side scatter (SS) value, which reflected the cellular hemoglobin of the red blood cell, to obtain FL4/SS for each red blood cell. The mean of FL4/SS values from all measured red blood cells of a blood sample was the mean of cellular HbA1c percentages of the sample, which correlated with the HbA1c percentage of the same blood sample obtained from the reference laboratory.

Figure 5A:
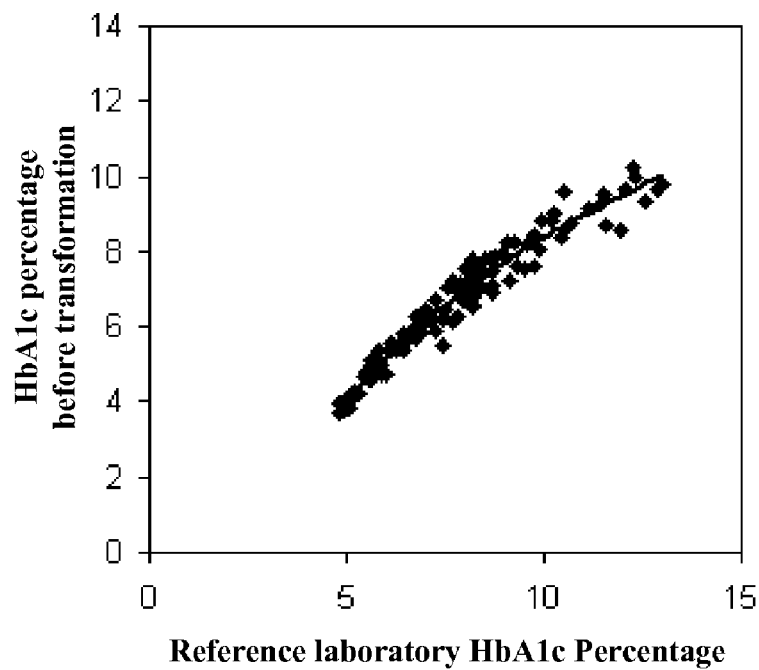
FIGS. 5A and 5B show the correlations of HbA1c percentages obtained using the instant method to the results reported by the standard methods from the reference laboratory before and after the mathematical transformation, respectively, as described in Example 7.

4. To normalize the FL4/SS values and bring them within the range of HbA1c percentage, the mean of the HbA1c percentage values from the three reference methods could be used (see Table 1A). This was done when a reference value of the labeled reference control was to be assigned. For a blood sample to be analyzed, the FL4/SS values could be normalized using the reference value of the labeled reference control (see Table 1B). FIG. 5A showed correlation of the normalized FL4/SS values with the percentage HbA1c values of the same blood samples obtained from the reference laboratory. It is noted that in Tables 1A and 1B, the FL4/SS value of the blood sample or the reference control is the mean of FL4/SS values of all measured cells or red cell analogs.

5. As shown in FIG. 5A, there was a slight non-linear correlation of the FL4/SS values with the results from the reference laboratory at the high end, which was believed due to steric hindrance among the conjugated antibody molecules within the cells, and was dependent on the antigen density in the cells. To correct this slight non-linear correlation at the high end, the normalized FL4/SS values were subjected to the following transformation:

$$\text{Transformed } FL4/SS \text{ value} = e^{0.157 \times \text{normalized } FL4/SS \text{ value}} + 1$$

This formula was valid in the range of FL4/SS values from approximately 3 to 15.

For reverse-transformation, the following formula was used:

$$\text{Normalized } FL4/SS \text{ value} = (LN(\text{transformed } FL4/SS \text{ value}) - 1)/0.157$$

Figure 5B:
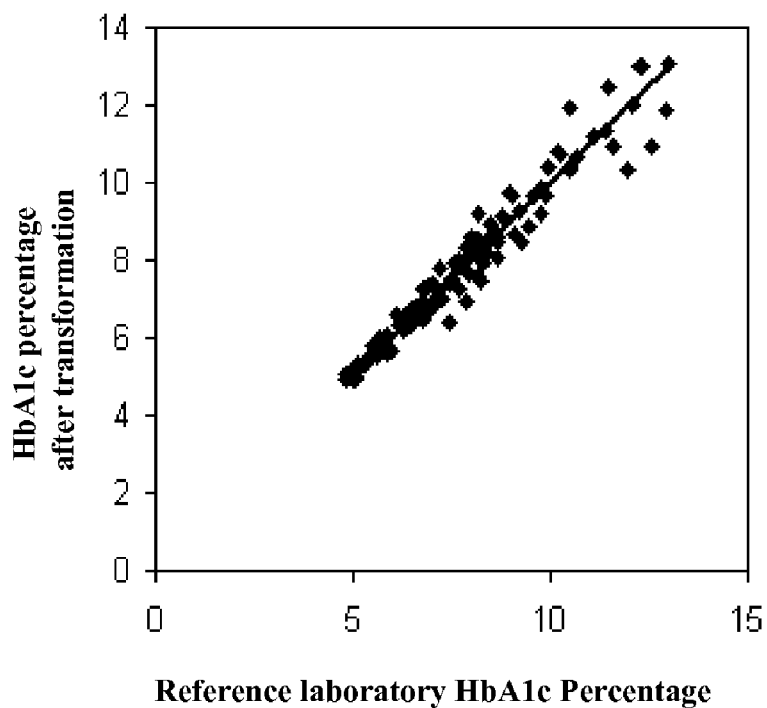

It should be understood that the above described formulas were adapted to the NGSP standardized HbA1c percentage data. The above transformation was developed empirically and which provided a better linear correlation with the HbA1c values from the reference laboratory (see FIGS. 5A and 5B). It is noted that several mathematical transformations of the flow cytometric data can be used to provide a linear correlation with the reference laboratory data. Preferably, a simple exponential formula shown above was used, because it was easy to transform or reverse-transform data as described herein.

The symbols used in the above described calculations are summarized in Tables 1A and 1B.

TABLE 1A

Assignment of a reference value of HbA1c percentage to the labeled reference control using blood samples with known HbA1c percentage values

| Parameter | Symbols |
|---|---|
| Corrected FL4/SS value of the blood sample | a |
| Corrected FL4/SS value of the labeled reference control | b |
| HbA1c percentage of the blood samples from the reference laboratory | c |
| Normalized FL4/SS value of the labeled reference control | $d = b * c^{reverse\text{-}transformed}$ |
| Assigned reference value of HbA1c percentage of the labeled reference control | $e = d^{transformed}$ |

TABLE 1B

Determination of HbA1c percentage of a blood sample using the reference value of the internal control

| Parameter | Symbols |
|---|---|
| Corrected FL4/SS value of the blood sample | a |
| Corrected FL4/SS value of the labeled reference control | b |
| reference value of HbA1c percentage of the labeled reference control | e |
| Normalized FL4/SS value of the blood sample | $f = a * e^{reverse\text{-}transformed}/b$ |
| HbA1c percentage of the blood sample | $g = f^{transformed}$ |

Using HbA1c percentage values of the first series of blood samples from the reference laboratory, a reference value of HbA1c percentage of the labeled reference control was assigned according to Table 1A as follows:

the mean corrected FS/SS of 20 samples, (a)=6.19;

the mean corrected FS/SS of labeled reference control in the 20 samples, (b)=7.63;

the mean reference laboratory HbA1c percentage values of the 20 samples, (c)=7.13;

the mean of the reverse transformed reference laboratory HbA1c percentage values of the 20 samples, $c^{reverse\text{-}transformed}$=6.01;

the mean normalized corrected FS/SS of the labeled reference control in the 20 samples, (d)=7.63*6.01/6.19=7.41;

the assigned reference value of HbA1c percentage of the labeled reference control, (e)=$d^{transformed}$=8.70.

Using the assigned reference value of HbA1c percentage (e) of the labeled reference control, the HbA1c percentage (g) of each blood sample of the three series was calculated according to Table 1B and the results were shown in Table 2. As defined previously, the HbA1c percentage (g) of a blood sample is the mean of cellular HbA1c percentages. As described above, the first series blood samples were used to assign the reference value to the reference control, therefore, the HbA1c percentage of the first series was calculated as a control group in the evaluation.

TABLE 2

Calculation of HbA1c percentages of the samples for the three series of samples

| Sample # | a | b | f | g |
|---|---|---|---|---|
| | First Series | | | |
| 1 | 7.15 | 7.53 | 7.03 | 8.2 |
| 2 | 4.19 | 7.9 | 3.93 | 5.04 |
| 3 | 6.8 | 7.71 | 6.54 | 7.59 |
| 4 | 4.06 | 7.64 | 3.93 | 5.04 |
| 5 | 7.4 | 7.93 | 6.91 | 8.05 |
| 6 | 6.69 | 7.65 | 6.48 | 7.51 |
| 7 | 4.47 | 7.8 | 4.25 | 5.3 |
| 8 | 6.97 | 7.4 | 6.98 | 8.13 |
| 9 | 8.16 | 7.48 | 8.08 | 9.67 |
| 10 | 6.07 | 7.64 | 5.88 | 6.84 |
| 11 | 5.96 | 7.6 | 5.81 | 6.76 |
| 12 | 5.92 | 7.53 | 5.82 | 6.78 |
| 13 | 6.94 | 7.43 | 6.92 | 8.05 |
| 14 | 5.16 | 7.92 | 4.82 | 5.8 |
| 15 | 6.68 | 7.37 | 6.72 | 7.81 |
| 16 | 5.48 | 7.53 | 5.39 | 6.33 |
| 17 | 5.86 | 7.9 | 5.49 | 6.44 |
| 18 | 8.44 | 7.32 | 8.55 | 10.4 |
| 19 | 6.03 | 7.71 | 5.79 | 6.75 |
| 20 | 5.47 | 7.55 | 5.37 | 6.31 |
| Mean | 6.19 | 7.63 | 6.03 | 7.14 |
| | Second Series | | | |
| 1 | 5.95 | 7.09 | 6.22 | 7.22 |
| 2 | 7 | 7.32 | 7.08 | 8.27 |
| 3 | 6.03 | 7.17 | 6.23 | 7.23 |
| 4 | 7 | 7.16 | 7.24 | 8.47 |
| 5 | 3.79 | 7.4 | 3.79 | 4.93 |
| 6 | 8.69 | 6.78 | 9.5 | 12.07 |
| 7 | 5.28 | 7.06 | 5.54 | 6.49 |
| 8 | 7.78 | 6.91 | 8.35 | 10.08 |
| 9 | 5.2 | 6.88 | 5.6 | 6.55 |
| 10 | 3.65 | 7.04 | 3.85 | 4.97 |
| 11 | 7.05 | 6.56 | 7.96 | 9.48 |
| 12 | 3.6 | 7.18 | 3.71 | 4.87 |
| 13 | 5.6 | 7.06 | 5.88 | 6.85 |
| 14 | 6.54 | 6.95 | 6.97 | 8.12 |
| 15 | 6.23 | 6.8 | 6.8 | 7.9 |
| 16 | 7.44 | 6.35 | 8.68 | 10.62 |
| 17 | 4.12 | 7.23 | 4.22 | 5.27 |
| 18 | 6.88 | 6.7 | 7.61 | 8.97 |
| 19 | 6.05 | 7.34 | 6.11 | 7.09 |
| 20 | 8.24 | 6.23 | 9.8 | 12.67 |
| Mean | 6.11 | 6.96 | 6.56 | 7.91 |
| | Third Series | | | |
| 1 | 9.54 | 8.03 | 8.8 | 10.83 |
| 2 | 5.77 | 7.94 | 5.38 | 6.33 |
| 3 | 6.55 | 7.74 | 6.27 | 7.27 |
| 4 | 10.35 | 7.67 | 10 | 13.06 |
| 5 | 5.36 | 7.91 | 5.02 | 5.98 |
| 6 | 7.73 | 7.84 | 7.3 | 8.55 |
| 7 | 9.42 | 7.98 | 8.74 | 10.72 |
| 8 | 6.56 | 7.83 | 6.21 | 7.21 |
| 9 | 7.53 | 7.85 | 7.11 | 8.3 |
| 10 | 8.13 | 7.04 | 8.55 | 10.41 |
| 11 | 5.9 | 7.97 | 5.49 | 6.43 |
| 12 | 4.19 | 8.08 | 3.84 | 4.97 |
| 13 | 7.39 | 7.94 | 6.9 | 8.03 |
| 14 | 8.46 | 8.31 | 7.54 | 8.88 |
| 15 | 4.2 | 7.85 | 3.97 | 5.07 |
| 16 | 8.17 | 7.76 | 7.79 | 9.24 |
| 17 | 7.51 | 7.74 | 7.2 | 8.41 |
| 18 | 4.92 | 7.89 | 4.62 | 5.62 |
| 19 | 6.11 | 7.78 | 5.82 | 6.77 |
| 20 | 5.1 | 8.03 | 4.71 | 5.69 |
| Mean | 6.94 | 7.86 | 6.56 | 7.89 |

To demonstrate the utility of the labeled reference control, a similar determination of HbA1c percentages was performed without using the labeled reference control. In the first series, the 20 corrected FS/SS values were normalized using their mean value (a) and the mean of the 20 reverse-transformed reference laboratory values ($c^{reverse-transformed}$) with the equation of (f)=(mean of $c^{reverse-transformed}$)/(mean of a); (g) was calculated by transformation of (f). Using the normalization factor of the first series for the second and the third series, the following results were obtained and compared with the results of the three series utilizing the labeled reference control (Table 3).

Furthermore, taking the first series as the reference and calculating the data of the second and third series with and without using the labeled reference control as the internal control, the ratio of the mean of obtained HbA1c percentage values to the reference laboratory values were obtained and shown in Table 4.

TABLE 3

Mean of HbA1c percentages of the three series of blood samples

| Series | Mean without the internal control | Mean with the internal control | Reference laboratory values |
|---|---|---|---|
| 1 | 7.09 | 7.14 | 7.13 |
| 2 | 7.05 | 7.91 | 8.05 |
| 3 | 8.10 | 7.89 | 7.85 |

TABLE 4

| Series | Ratio without the internal control | Ratio with the internal control |
|---|---|---|
| 1 | 1.0 | 1.0 |
| 2 | 0.88 | 0.98 |
| 3 | 1.03 | 1.01 |

Moreover, the standard deviation of the results of the three series without the internal control was 0.079, while the standard deviation of the results of the three series with the internal control was 0.015.

EXAMPLE 8

Correction of Intra Assay Variation in Measurement of the Percentage of HbA1c Using the Reference Control To analyze the intra assay variation, the data obtained from the three series of blood samples in Example 7 were further analyzed.

Figure 6A:
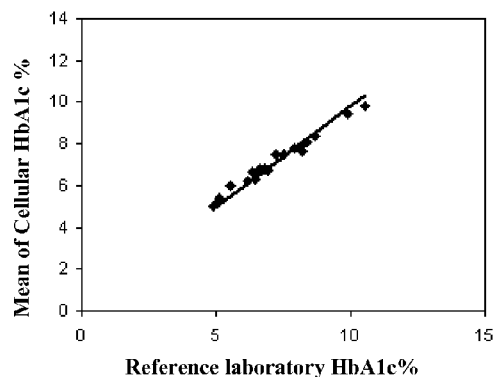
FIGS. 6A thru 6F show the correlations of HbA1c percentages obtained using the instant method to the results reported by the standard methods from the reference laboratory without and with the use of the internal control, respectively, as described in Example 8.
Figure 6B:
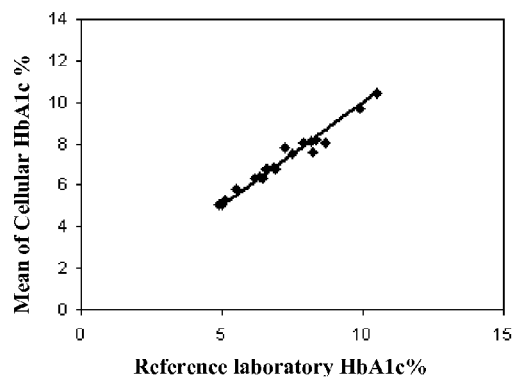
Figure 6C:
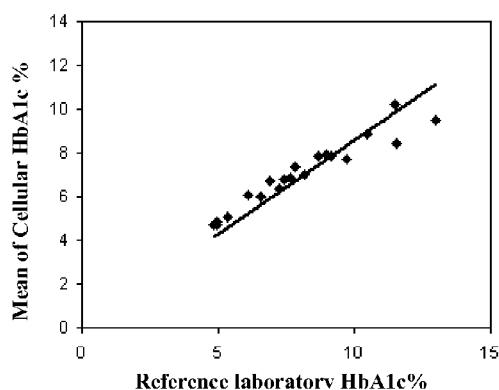
Figure 6D:
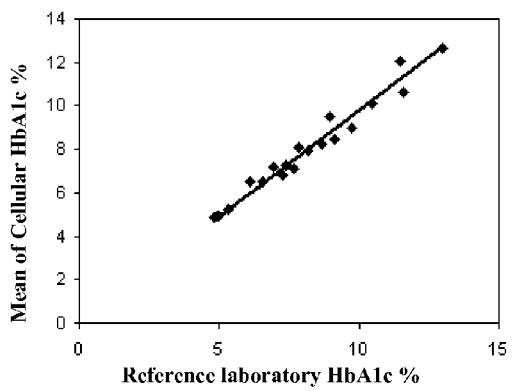
Figure 6E:
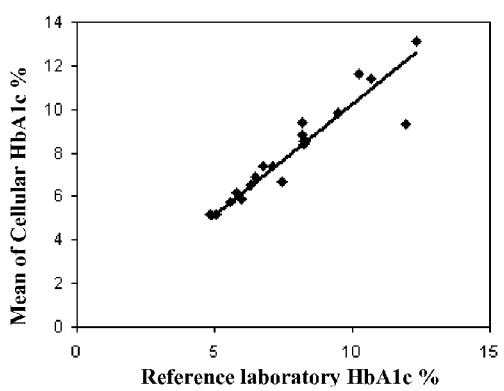
Figure 6F:
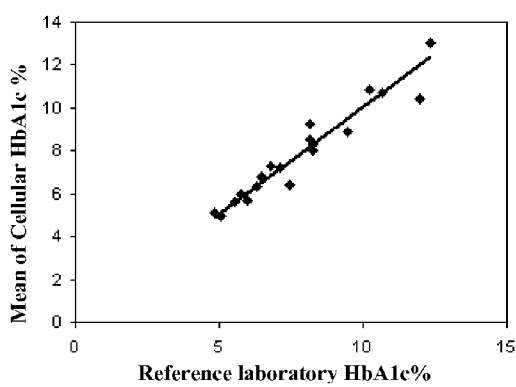

The HbA1c percentages obtained using the instant method, with and without utilizing the labeled reference control as the internal control, were plotted against the HbA1c percentages reported by the reference laboratory, as shown in FIGS. 6A thru 6F. FIGS. 6A and 6B showed the correlation curves of the first series of the blood samples. FIGS. 6C and 6D, and FIGS. 6E and 6F showed the correlation curves of the second series and the third series, respectively. Among these, FIGS. 6A, 6C and 6E showed the correlation curves of the HbA1c percentages obtained using the instant method without using the internal control. FIGS. 6B, 6D and 6F showed the correlation curves of the HbA1c percentages obtained using the instant method utilizing the internal control.

Of each experiment the best fitted straight line was drawn through the origin. The correlation coefficient ($r^2$) and the slope (y) of the correlation curves were shown in Table 5. The intercept (x) is zero.

TABLE 5

| Series | $r^2$ Without the internal control | $r^2$ With the internal control | y Without the internal control | y With the internal control |
|---|---|---|---|---|
| 1 | 0.9469 | 0.9609 | 0.9872 | 0.9972 |
| 2 | 0.8075 | 0.9661 | 0.8589 | 0.9796 |
| 3 | 0.8662 | 0.9275 | 1.0270 | 1.0026 |

The results showed that the HbA1c percentages of blood samples obtained using the instant method with the labeled reference control as an internal control correlated to the results from the existing reference methods substantially better than the results obtained without using the internal control. Therefore, using the instant internal control improved intra assay consistency.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A reference control for cell by cell analysis on a flow cytometric analyzer, comprising
    cellular analogs, wherein said cellular analogs comprise permeated blood cells containing therein aggregated intracellular proteins and one or more preserved antigenic sites thereof, and cellular membrane permeable to an antibody; and
    a suspension medium, wherein said suspension medium does not contain glycerol or dimethylsulfoxide,
    said reference control is freeze-thaw stable and can undergo one or more cycles of freezing and thawing, wherein said cellular analogs maintain said one or more preserved antigenic sites of said proteins after being thawed.

2. The reference control of claim 1, wherein said blood cells have a normal or abnormal level of an antigen of interest.

3. The reference control of claim 1, wherein said blood cells are mammalian, avian, or reptilian blood cells.

4. The reference control of claim 1, wherein said cellular analogs are red cell analogs comprising permeated red blood cells having preserved antigenic sites of one or more hemoglobin variants.

5. The reference control of claim 1, wherein said cellular analogs further comprise a cellular marker bound to one or more cellular components of said permeated blood cells.

6. The reference control of claim 5, wherein said cellular marker is a fluorescent dye.

7. The reference control of claim 6, wherein said fluorescent dye is carboxyfluorescein succinimidyl ester (CFSE).

8. The reference control of claim 7, wherein said cellular analogs are red cell analogs comprising permeated red blood cells having preserved antigenic sites of one or more hemoglobin variants.

9. The reference control of claim 8, wherein said reference control is frozen and said cellular analogs maintain said preserved antigenic sites of said one or more hemoglobin variants after being thawed.

10. The reference control of claim 1, wherein said suspension medium comprises a saccharide.

11. The reference control of claim 10, wherein said saccharide comprises sucrose.

12. The reference control of claim 1, wherein said suspension medium does not contain a phosphate salt.

13. The reference control of claim 1, wherein said permeated blood cells are unfixed.

14. The reference control of claim 1, wherein said permeated blood cells are spheroid.

15. The reference control of claim 1, wherein said cellular analogs maintain said permeable cellular membrane after being thawed.

* * * * *